US006626918B1

United States Patent
Ginn et al.

(10) Patent No.: US 6,626,918 B1
(45) Date of Patent: Sep. 30, 2003

(54) APPARATUS AND METHODS FOR POSITIONING A VASCULAR SHEATH

(75) Inventors: Richard S. Ginn, San Jose, CA (US); W. Martin Belef, San Jose, CA (US)

(73) Assignee: Medical Technology Group, Santa Clara, CA (US)

( * ) Notice: Subject to any disclaimer, the term of this patent is extended or adjusted under 35 U.S.C. 154(b) by 215 days.

(21) Appl. No.: 09/680,837

(22) Filed: Oct. 6, 2000

(51) Int. Cl.[7] .............................................. A61B 17/08
(52) U.S. Cl. ....................... 606/148; 606/213; 606/142
(58) Field of Search ................................ 606/213, 219, 606/220, 139, 146, 142, 143, 144, 148

(56) References Cited

U.S. PATENT DOCUMENTS

| | | | |
|---|---|---|---|
| 1,596,004 A | | 8/1926 | Bengoa |
| 4,162,673 A | | 7/1979 | Patel |
| 4,215,699 A | | 8/1980 | Patel |
| 4,961,729 A | | 10/1990 | Vaillanocurt |
| 5,192,302 A | * | 3/1993 | Kensey et al. .............. 606/213 |
| 5,217,024 A | | 6/1993 | Dorsey et al. |
| 5,222,974 A | * | 6/1993 | Kensey et al. .............. 606/213 |
| 5,226,908 A | | 7/1993 | Yoon |
| 5,304,184 A | * | 4/1994 | Hathaway et al. .......... 606/144 |
| 5,383,896 A | | 1/1995 | Gershoney et al. |
| 5,413,571 A | | 5/1995 | Katsaros et al. |
| 5,419,777 A | * | 5/1995 | Hofling ....................... 604/264 |
| 5,431,639 A | | 7/1995 | Shaw |
| 5,437,631 A | | 8/1995 | Janzen |
| 5,507,744 A | | 4/1996 | Tay et al. |
| 5,674,231 A | * | 10/1997 | Green et al. ................ 606/142 |
| 5,830,125 A | * | 11/1998 | Scribner et al. ............ 606/139 |
| 6,033,427 A | * | 3/2000 | Lee ............................. 606/213 |
| 6,117,125 A | * | 9/2000 | Rothbarth et al. .......... 604/523 |
| 6,197,042 B1 | * | 3/2001 | Ginn et al. ................. 606/213 |
| 6,383,208 B1 | * | 5/2002 | Sancoff et al. ............. 606/213 |
| 6,391,048 B1 | * | 5/2002 | Ginn et al. ................. 606/213 |
| 6,461,364 B1 | * | 10/2002 | Ginn et al. ................. 606/142 |

OTHER PUBLICATIONS

PCT Publication No. WO 00/07640, Steven J. Tallarida, "Vascular Suction Cannula, Dilator and Surgical Stapler", Feb. 17, 2000.

* cited by examiner

*Primary Examiner*—Michael J. Milano
*Assistant Examiner*—Jessica R Baxter
(74) *Attorney, Agent, or Firm*—Orrick, Herrington & Sutcliffe LLP; James W. Geriak

(57) ABSTRACT

An apparatus for positioning an introducer sheath includes a sheath having a distal end including first and second ports, the second port being located distally from the first port. An obturator is slidable within the sheath that includes a distal region that sealingly engages an interior surface of the sheath. The obturator includes first and second openings in the distal region that are alignable with the first and second ports in the sheath. A housing is slidable on the exterior of the sheath that releasably holds a closure element. The sheath may be inserted into an incision communicating with a blood vessel, the first and second ports providing backbleed indication of the depth of the insertion of the sheath into the vessel. The housing is actuated to deploy the closure element to engage and close the incision.

37 Claims, 16 Drawing Sheets

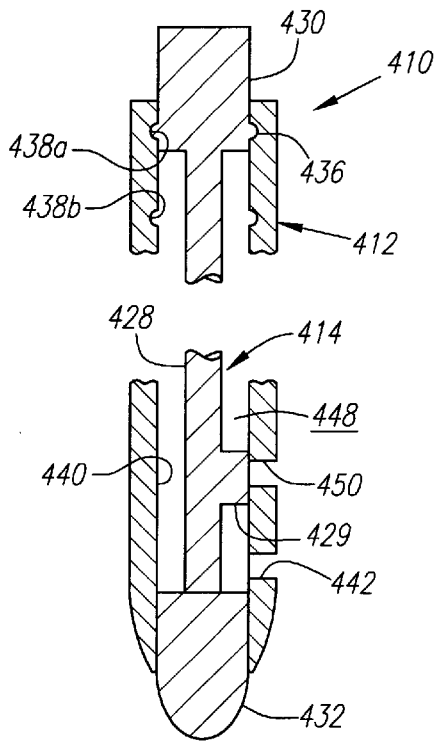
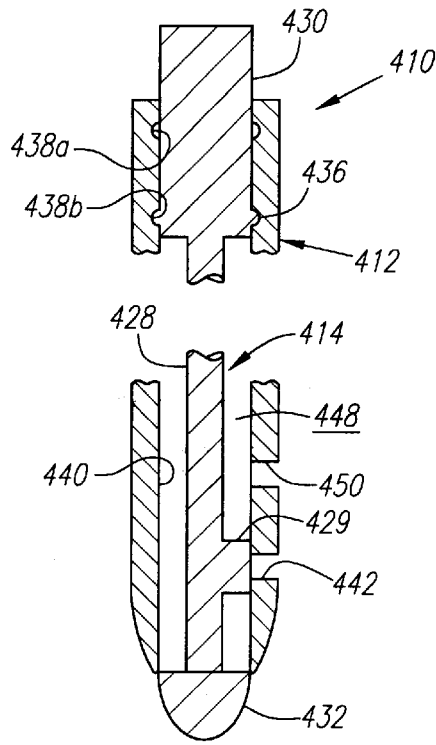
FIG. 15A  FIG. 15B
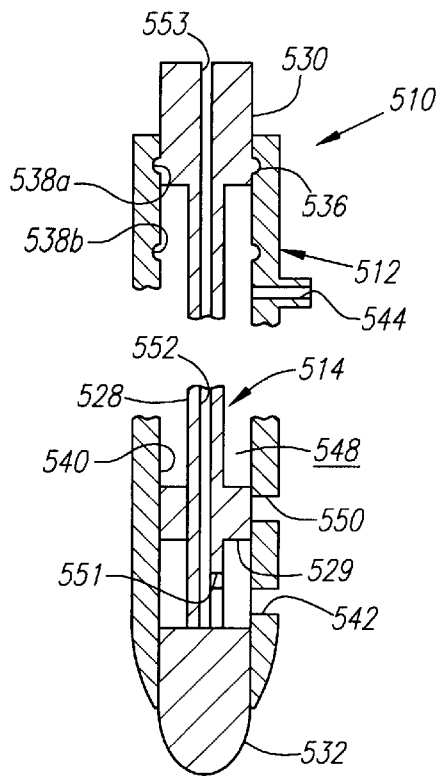
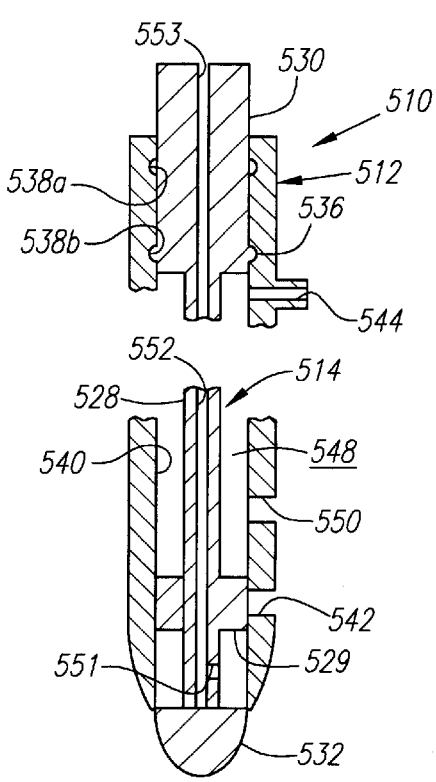
FIG. 16A  FIG. 16B

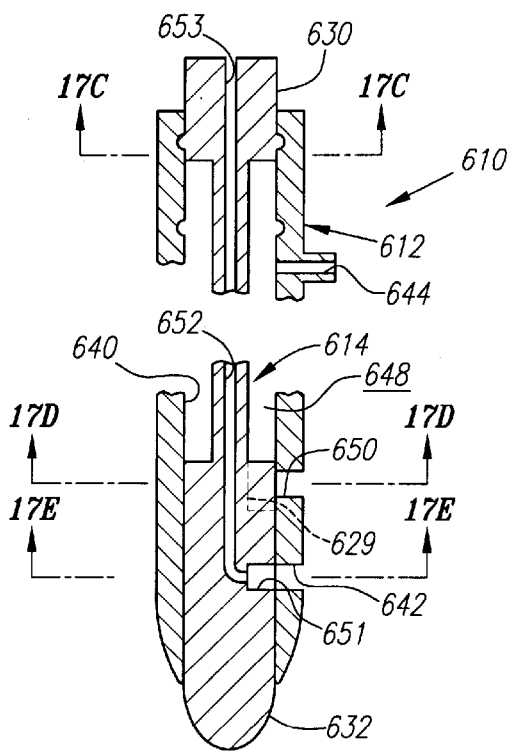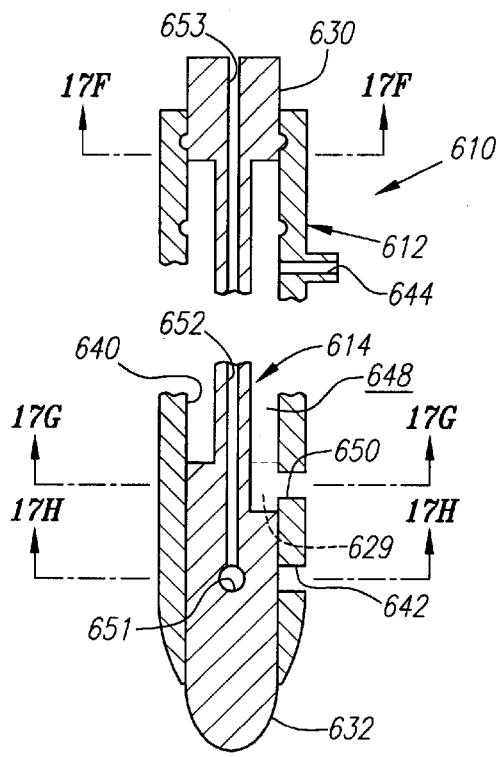
FIG. 17A    FIG. 17B
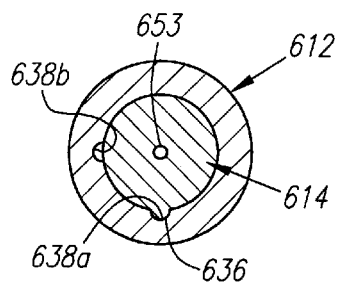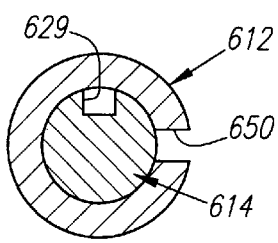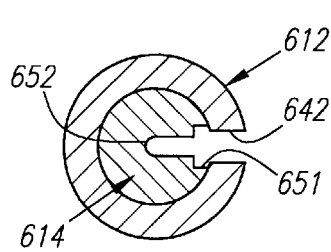
FIG. 17C    FIG. 17D    FIG. 17E
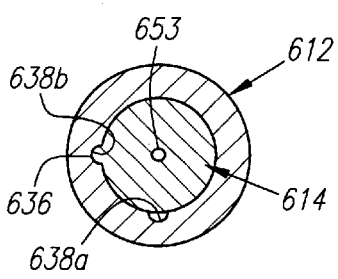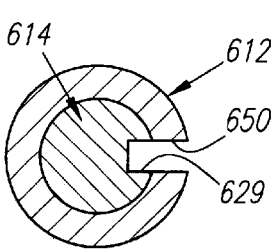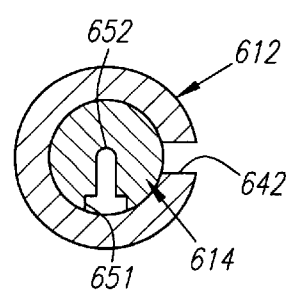
FIG. 17F    FIG. 17G    FIG. 17H

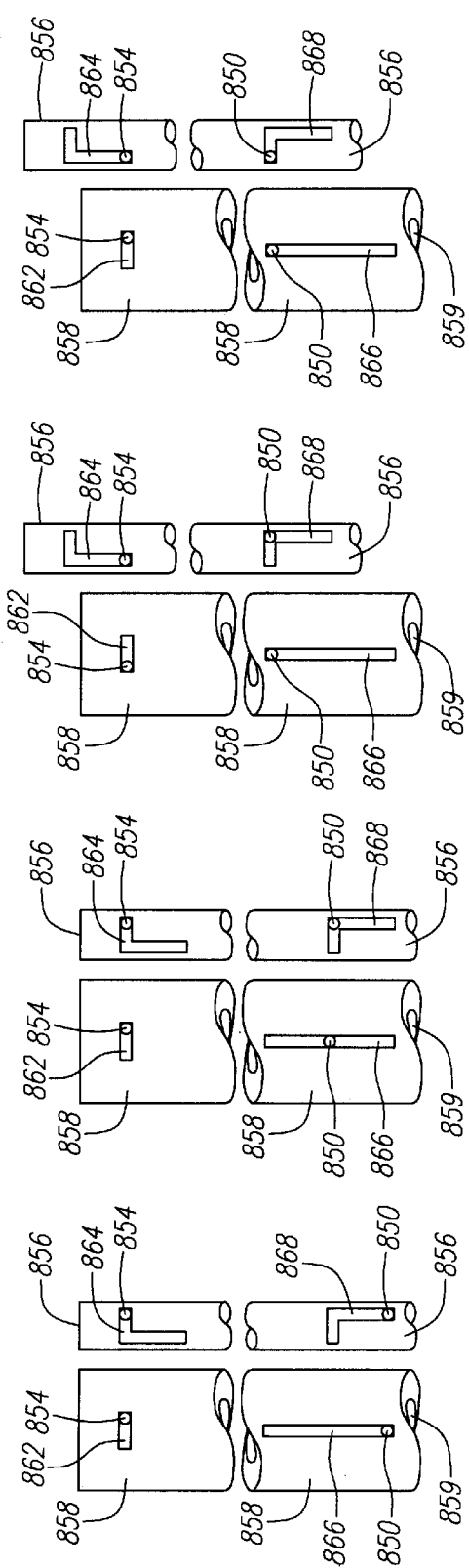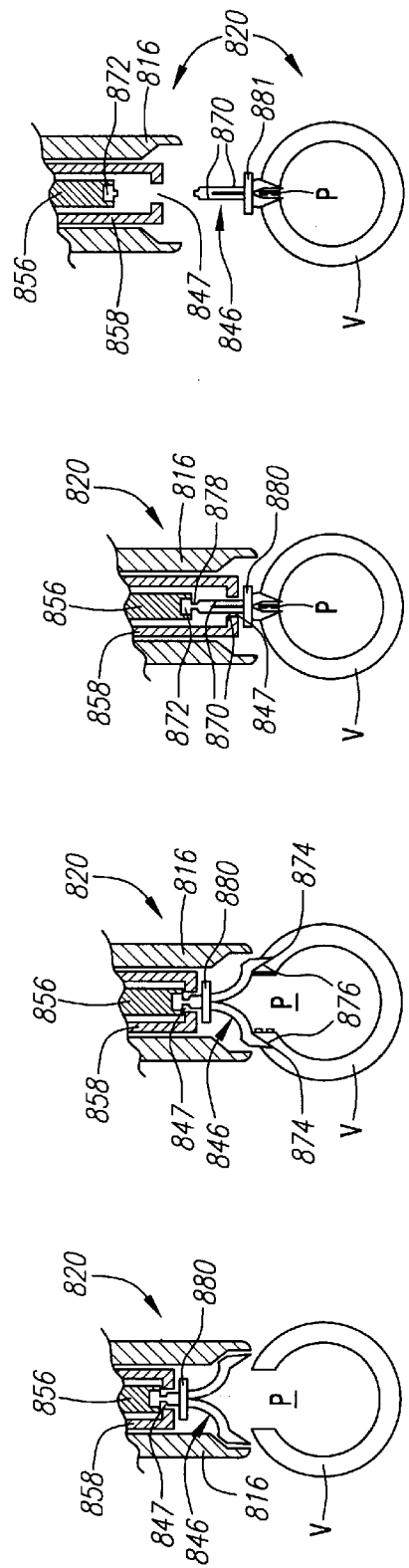

APPARATUS AND METHODS FOR POSITIONING A VASCULAR SHEATH

FIELD OF THE INVENTION

The present invention relates generally to apparatus and methods for closing and/or sealing openings into body lumens, and more particularly to apparatus and methods for delivering a vascular closure element for closing an iatrogenic puncture in a blood vessel formed during a diagnostic or therapeutic procedure.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel. A catheter may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the catheter and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

To facilitate positioning devices that are percutaneously inserted into a blood vessel, "backbleed" indicators have been suggested. For example, U.S. Pat. No. 4,317,445, issued to Robinson, discloses a flashback chamber on a first end of a cannula that communicates with a port on a second end. The second end is percutaneously introduced into a patient until the port enters the vessel, whereupon blood, under normal blood pressure, may advance along the cannula and enter the flashback chamber, thereby providing a visual indication that the vessel has been entered. This reference, however, does not discuss vascular wound closure, but is merely directed to an introducer device. In contrast, U.S. Pat. No. 5,676,974, issued to Kensey et al., discloses a back bleed lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating the deployment and deflection of a surgical clip against the vessel wall. Such a device, however, may risk engagement between the loop and the surgical clip, thereby preventing the loop from a being withdrawn from the vessel.

Accordingly, apparatus and methods for vascular puncture closure that are simpler to manufacture and/or use, or that overcome the disadvantages of known devices would be considered useful.

SUMMARY OF THE INVENTION

The present invention is directed to apparatus and methods for providing access into a blood vessel or other body lumen from an incision or puncture, and/or for delivering a closure element for closing the incision.

In accordance with one aspect of the present invention, an apparatus is provided that includes a sheath having proximal and distal ends, the distal end having a size and shape for insertion into a body lumen. The distal end includes first and second ports therein, the second port being disposed at a more distal location than the first port. An obturator is disposed within the sheath, the obturator including a distal region having a size for sealingly engaging an interior surface of the sheath. The obturator includes first and second openings in the distal region, the first and second openings being alignable with the first and second ports in the sheath. First and second lumens extend distally from the proximal end of at least one of the sheath and the obturator, the first and second lumens communicating with the first and second openings, respectively. One or more of the lumens may be located within the wall of one of the sheath or obturator, or may be defined by a region between the sheath and obturator.

In addition, the apparatus may include a closure element slidably disposed on an exterior of the sheath, the closure element configured for engaging tissue adjacent an opening into a body lumen for closing the opening. Preferably, a housing is slidably disposed on the exterior of the sheath, the housing configured for releasably holding the closure element. The housing may be actuable from a proximal end of the sheath for advancing the closure element distally during deployment of the closure element.

In a preferred embodiment, the first and second ports are axially aligned with one another. A marker may then be provided on the proximal end of the tubular sheath, the marker having a let predetermined peripheral orientation about the sheath for identifying the peripheral location of the first and second ports.

During use, the obturator may be inserted into the sheath, and the first and second ports may be aligned with the first and second openings when the obturator is fully inserted into the sheath. The obturator and the sheath may include cooperating detents for securing the obturator axially with respect to the sheath when the obturator is fully inserted into the sheath. Alternatively, the first opening may be aligned with the first port when the obturator is inserted a first distance into the sheath, and the second opening may be aligned with the second port when the obturator is inserted a second distance into the sheath.

In one embodiment, the first and second lumens may extend within the obturator between its proximal end and the first and second openings, respectively. Alternatively, the second lumen may extend axially through the obturator, and the first lumen may be defined by an annular lumen between the obturator and the sheath.

In accordance with another aspect of the present invention, an apparatus is provided for delivering a vascular closure element into engagement with tissue adjacent an opening into a body lumen. The apparatus includes a sheath having proximal and distal ends and an exterior surface. The sheath includes an interior surface defining a first lumen extending between the proximal and distal ends, and one or more ports in the distal end communicating with the first lumen. A housing is slidably disposed on the exterior of the sheath, the housing being configured for releasably holding a closure element. The housing is actuable from a proximal end of the sheath for advancing the closure element distally during deployment of the closure element.

An obturator is insertable into the first lumen of the sheath, the obturator including a distal region configured for sealingly engaging the interior surface of the sheath, thereby defining an annular region between the obturator and the sheath proximal to the distal region. The annular region may communicate with the one or more ports when the obturator is fully inserted into the sheath. A backbleed port may be provided on the proximal end of the sheath, the backbleed port communicating with the first lumen.

In accordance with yet another aspect of the present invention, an apparatus is provided for introduction into an opening in a wall of a body lumen. The apparatus includes a sheath having proximal and distal ends, the distal end having a size and shape for insertion into a body lumen. The distal end of the sheath includes first and second ports therein, the second port being disposed at a more distal location than the first port. The sheath may include a clip housing, a peripheral marker or other features, similar to the embodiments described above.

An obturator is disposed within the sheath, the obturator including a distal region having a size for sealingly engaging an inner surface of the sheath. The obturator is movable with respect to the sheath for selectively opening and closing the first and second side ports to permit fluid flow therethrough to the proximal end of the sheath. In one embodiment, the obturator at least partially defines a first lumen extending from the proximal end of the sheath towards the distal region of the obturator. The obturator preferably includes a region for selectively sealing the first and second ports in the sheath, whereby only one of the first and second ports communicates with the first lumen.

Preferably, the first lumen is defined between the obturator and the inner surface of the sheath. The obturator may include a second lumen therein having an inlet proximal to the distal region of the obturator and a piston for sealingly engaging the inner surface of the sheath. The piston may be located proximal to the inlet, whereby the second lumen communicates with the second side port when the obturator is disposed at a first position, and the first lumen communicates with the first side port when the obturator is disposed at a second position. The obturator may movable axially or rotated with respect to the sheath between the first and second positions.

Other objects and features of the present invention will become apparent from consideration of the following description taken in conjunction with the accompanying drawings.

BRIEF DESCRIPTION OF THE DRAWINGS

FIGS. 15A and 15B are cross-sectional views of a vascular sheath and obturator, showing first and second side ports in the sheath being selectively opened, respectively.

FIGS. 16A and 16B are cross-sectional views of an alternative embodiment of a vascular sheath and obturator, showing first and second side ports in the sheath being selectively opened, respectively.

FIGS. 17A and 17B are cross-sectional views of yet another alternative embodiment of a vascular sheath and obturator, showing first and second side ports in the sheath being selectively opened, respectively.

FIGS. 17C through 17H are cross-sectional views of the vascular sheath and obturator of FIGS. 17A and 17B.

FIGS. 21A–21B through 24A–24B are side-sectional views of the closure component in use at a vascular puncture site.

DETAILED DESCRIPTION OF THE PREFERRED EMBODIMENTS

Figure 1:
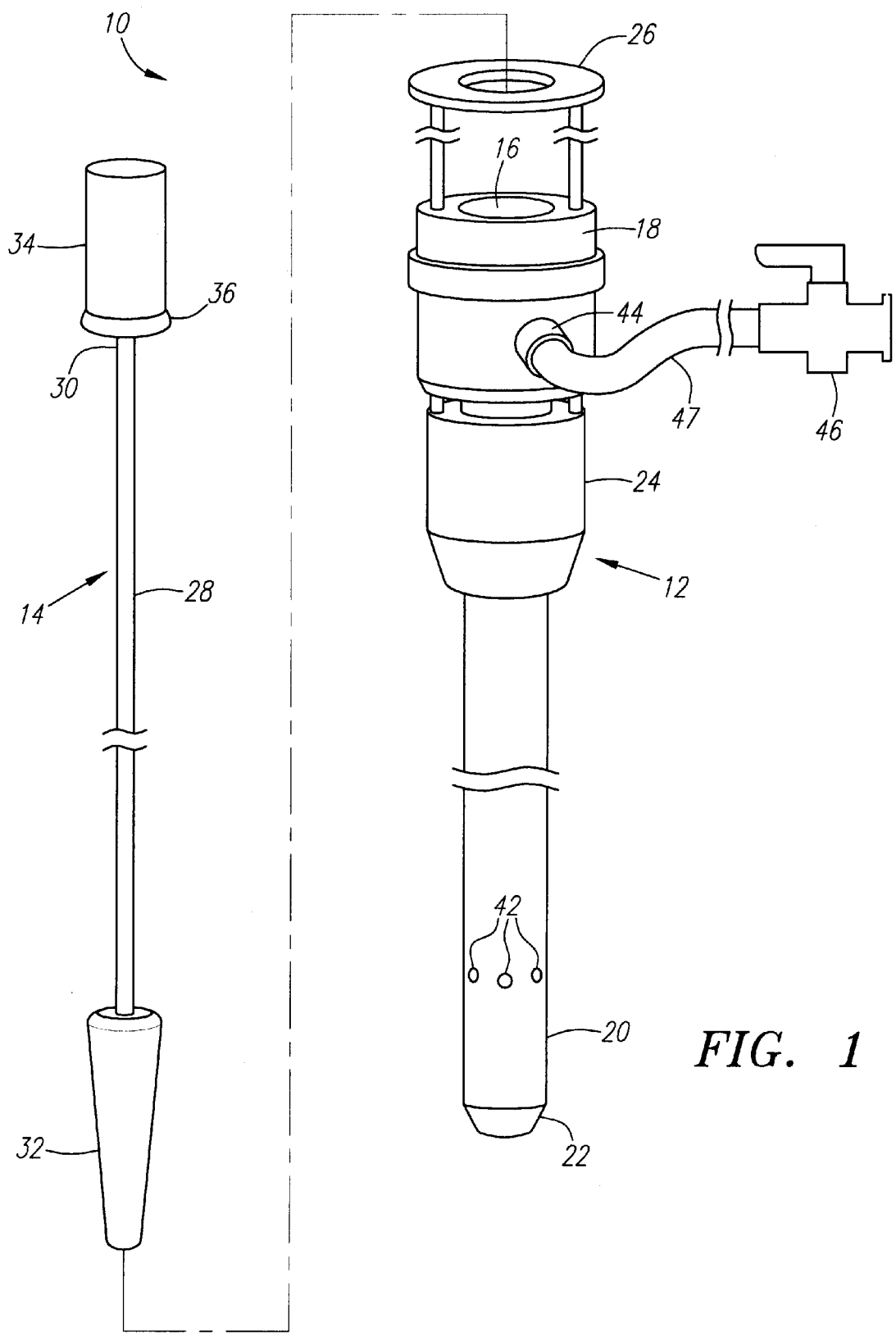
FIG. 1 is a side view of a first preferred embodiment of a vascular sheath and obturator, including a clip delivery device, in accordance with the present invention.

Turning now to the drawings, FIGS. 1–5 show a first preferred embodiment of an apparatus 10 for providing access into a blood vessel 90 or other body lumen from an incision or puncture 92 and/or for delivering a closure element (not shown) for closing the incision 92. Generally, the apparatus 10 includes a vascular sheath 12 and an obturator 14. The sheath 12 is a substantially flexible or semi-rigid tubular body including a lumen 16 extending between its proximal and distal ends 18, 20. The distal end 20 has a size and shape to facilitate insertion into a blood vessel, e.g., having a tapered tip 22 for facilitating substantially atraumatic introduction through the incision 92 and partial insertion into the vessel 90. The lumen 16 has a size to accommodate insertion of endoluminal devices therethrough, such as a catheter, guidewire, and the like (not shown).

A housing 24 is slidably disposed on an exterior of the sheath 12, the housing 24 configured for releasably holding a closure element (not shown). In a preferred embodiment, the closure element is an annular-shaped clip (not shown), including one or more barbs for engaging the tissue around the incision 92 adjacent to the wall 98 of the vessel 90. Preferably, the clip is configured for drawing the tissue around the incision 92 at the wall 98 of the vessel 90 substantially closed and/or for enhancing hemostasis within the incision 92.

The housing 24 is actuable from the proximal end 18 of the sheath 12, for example, by handle 26, for advancing the closure element distally during deployment, as described further below. Exemplary embodiments of a housing and closure element for use with an apparatus in accordance with the present invention are disclosed in co-pending application Ser. Nos. 09/478,179, filed Jan. 5, 2000, now U.S. Pat. No. 6,197,042, U.S. Ser. No. 09/546,998, filed Apr. 11, 2000, now U.S. Pat. No. 6,461,364, and U.S. Ser. No. 09/610,238, filed Jul. 5, 2000, now U.S. Pat. No. 6,391,048 the disclosures of which are expressly incorporated herein by reference.

The obturator 14 is a substantially flexible, or semi-rigid elongate body 28 having a proximal end 30 and an enlarged distal end 32. A handle 34 is provided on the proximal end 28 that includes an annular ridge 36 or other detent thereon that may engage a complementary-shaped pocket 38 or other cooperating detent in the sheath 12 for substantially securing the obturator 14 when it is disposed within the sheath 12, as described further below. The sheath 12 also preferably includes a seal (not shown), such as a hemostatic valve, within the lumen 16 at or near the proximal end 18 that provides a fluid-tight seal, yet accommodates insertion of devices, such as the obturator 14, into the lumen 16 without fluid passing proximally from the sheath 12.

The distal end 32 of the obturator 14 has a configuration for slidably, but sealably engaging an inner wall 40 of the sheath 12. The distal end 32 of the obturator 14 may also be substantially soft and/or flexible, possibly including a pigtail (not shown), to facilitate atraumatic advancement into a blood vessel. Alternatively, the distal end 32 of the obturator 14 may be expandable from a contracted configuration for facilitating insertion into the sheath 12 to an enlarged configuration for sealingly engaging the inner wall 40 of the sheath 12. For example, the distal end of the obturator 14 may be an inflatable balloon (not shown), and the obturator 14 may include an inflation lumen (also not shown) communicating from the proximal end 30 to an interior of the balloon for introducing fluid, such as saline, into the balloon to expand it into engagement with the inner wall 40 of the sheath 12.

Figure 2:
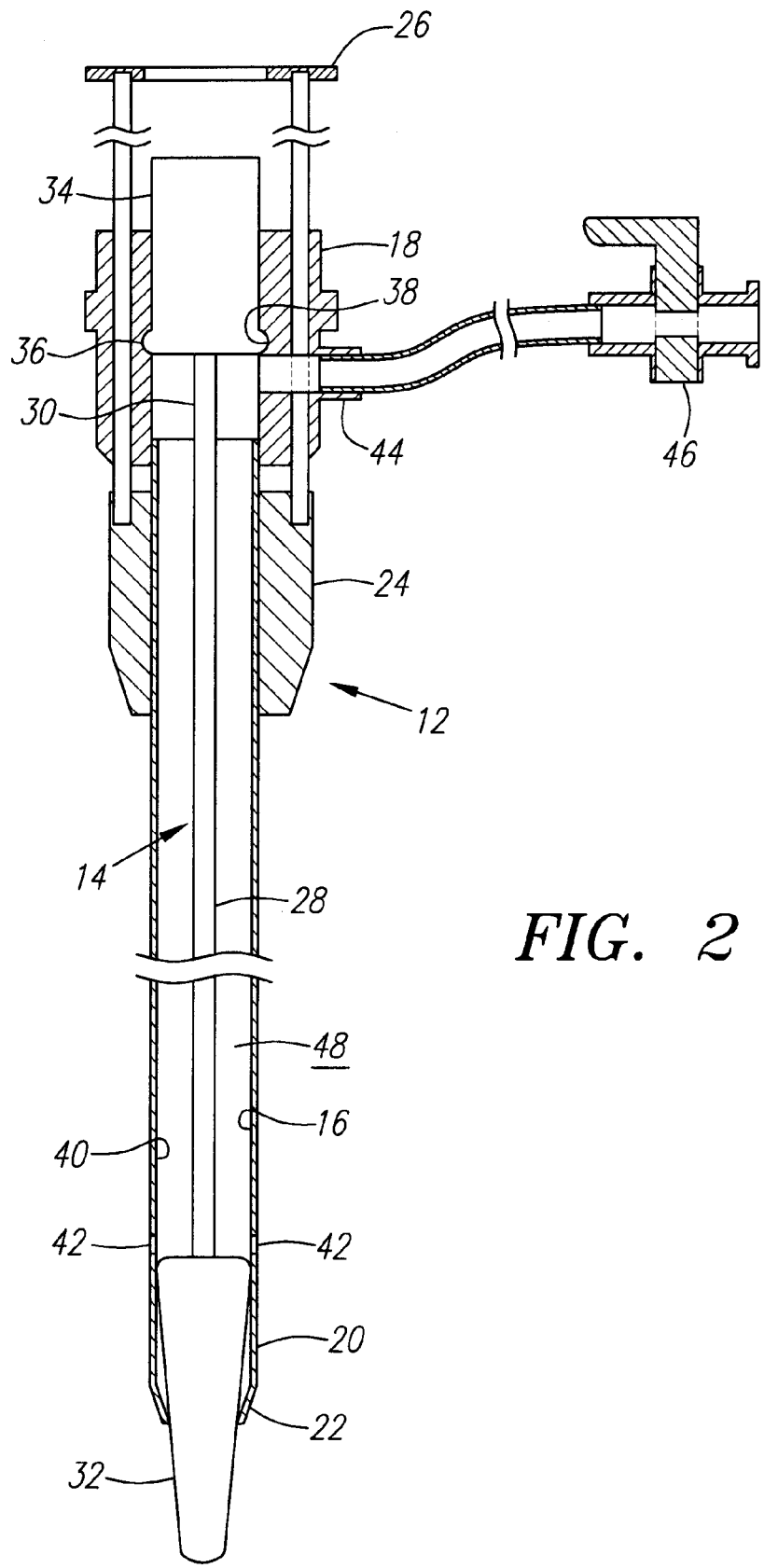
FIG. 2 is a cross-sectional view of the obturator and vascular sheath of FIG. 1, with the obturator fully inserted into the vascular sheath.

The sheath 12 includes one or more, and preferably a plurality of, distal side ports 42 at or near the distal end 20 that communicate with the lumen 16. The distal side ports 42 may be disposed circumferentially about a predetermined location with respect to the housing 24, as described further below. The sheath 12 also preferably includes a proximal side port 44 at or near the proximal end 18 that also communicates with the lumen 16, and also communicates with flush port 46, or other valve or backbleed indicator (not shown). As best seen in FIG. 2, when the obturator 14 is fully inserted into the lumen 16, the cooperating ridge and pocket 36, 38 engage one another to prevent inadvertent axial movement of the obturator 14 with respect to the sheath 12. In addition, the obturator 14 and sheath 12 together define an annular region 48 that communicates with both the distal and proximal side ports 42, 44 in the sheath 12.

Figure 3:
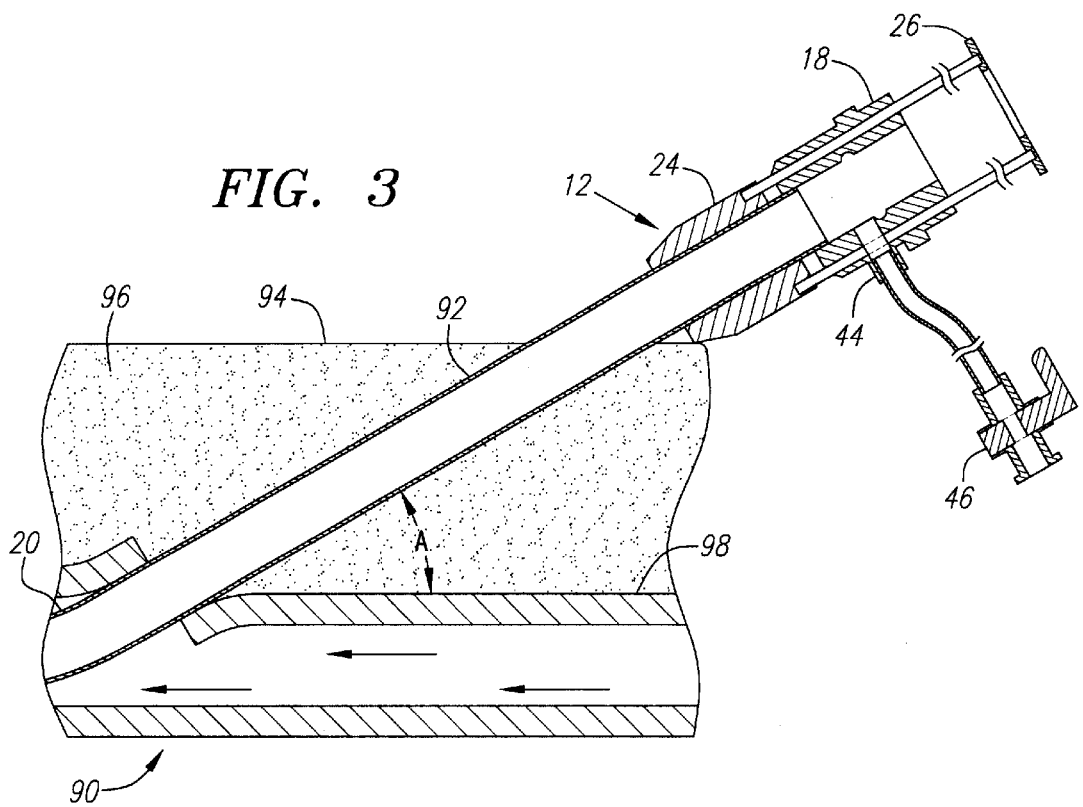
FIG. 3 is a cross-sectional view of the vascular sheath of FIG. 1 inserted through an incision into a blood vessel.

As best seen in FIG. 3, the sheath 12 may be inserted or otherwise positioned within a blood vessel 90, i.e., through an incision, puncture, or other opening 92 that extends from a patient's skin 94 through any intervening tissue 96, and a wall 98 of the vessel 90. The sheath 12 may be advanced over a guidewire or other rail (not shown) previously positioned through the incision 92 into the blood vessel 90 using a conventional procedure. Preferably, the blood vessel 90 is a peripheral vessel, such as a femoral or carotid artery, although other body lumens may be accessed using the sheath 12, as will be appreciated by those skilled in the art.

The incision 92, and-consequently the sheath 12, are preferably oriented at a substantially acute angle "A" with respect to the vessel 90, thereby facilitating introduction of devices through the lumen 16 of the sheath 12 into the vessel 90 with minimal risk of damage to the vessel 90. One or more devices, such as a guide wire, a catheter, and the like may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature.

Figure 4:
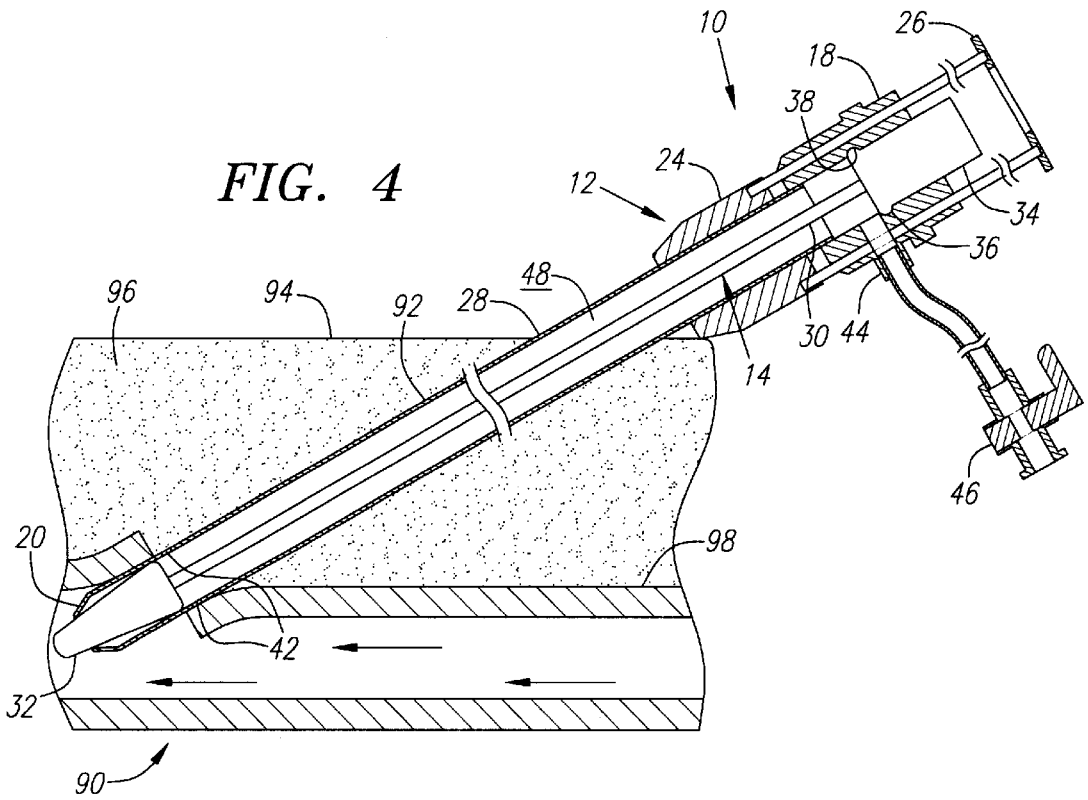
FIG. 4 is a cross-sectional view of the vascular sheath of FIG. 3 with the obturator of FIG. 1 fully inserted therein, showing side ports in the vascular sheath being disposed outside the blood vessel.

After the procedure is complete, the device(s) may be removed from the sheath 12, and the obturator 14 inserted through the hemostatic valve (not shown) into the lumen 16, e.g., until the distal end 32 extends beyond the distal end 20 of the sheath 12 and/or the cooperating detents 36, 38 are engaged, as shown in FIG. 4. Preferably, when the obturator 14 is fully inserted into the sheath 12, the distal side ports 42 communicate with the annular region 48. The sheath 12 and obturator 14 may then be moved in conjunction with one another, and preferably are together partially withdrawn from the vessel 90, as shown in FIG. 4. Preferably, the sheath 12 is positioned such that the distal side ports 42 are adjacent to and not within the vessel 90. Fluid, such as saline, may be directed into the flush port 46 to flush blood or other visible body fluid from the proximal side port 44.

Figure 5:
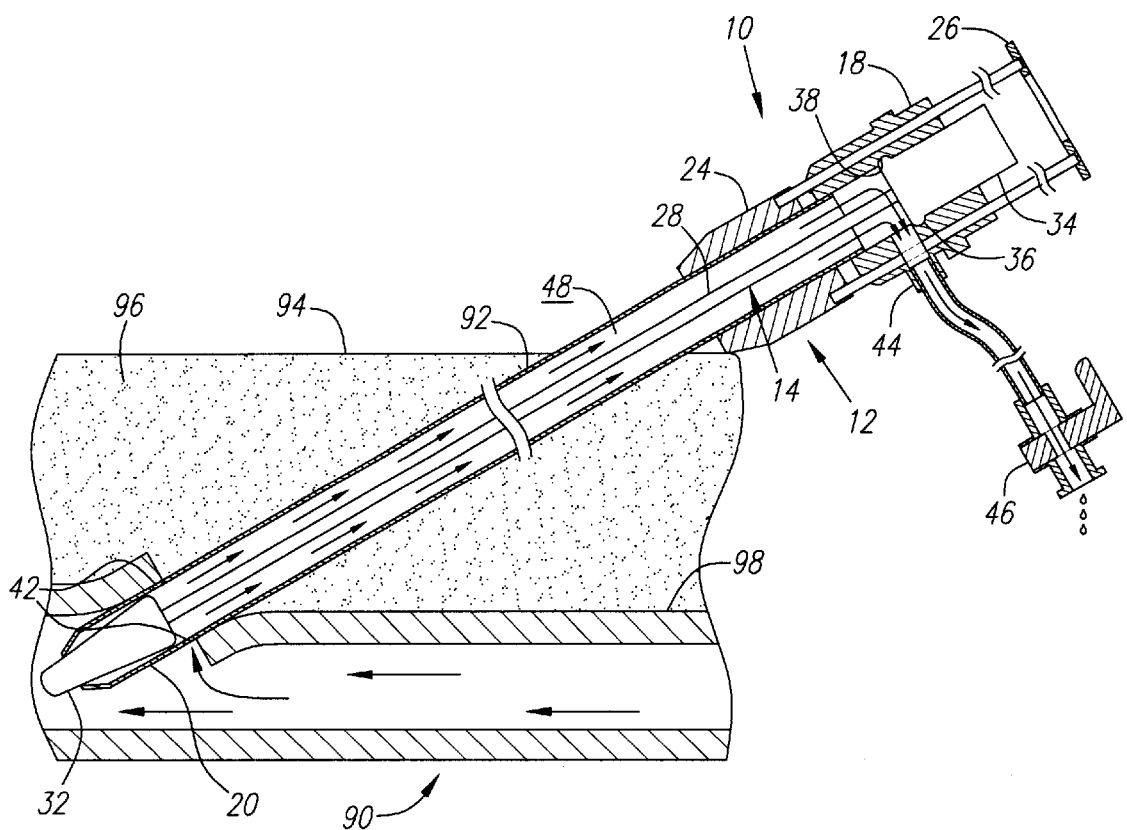
FIG. 5 is a cross-sectional view of the vascular sheath and obturator of FIG. 4 with the sheath advanced such that the side ports are disposed inside the blood vessel.
Figure 6:
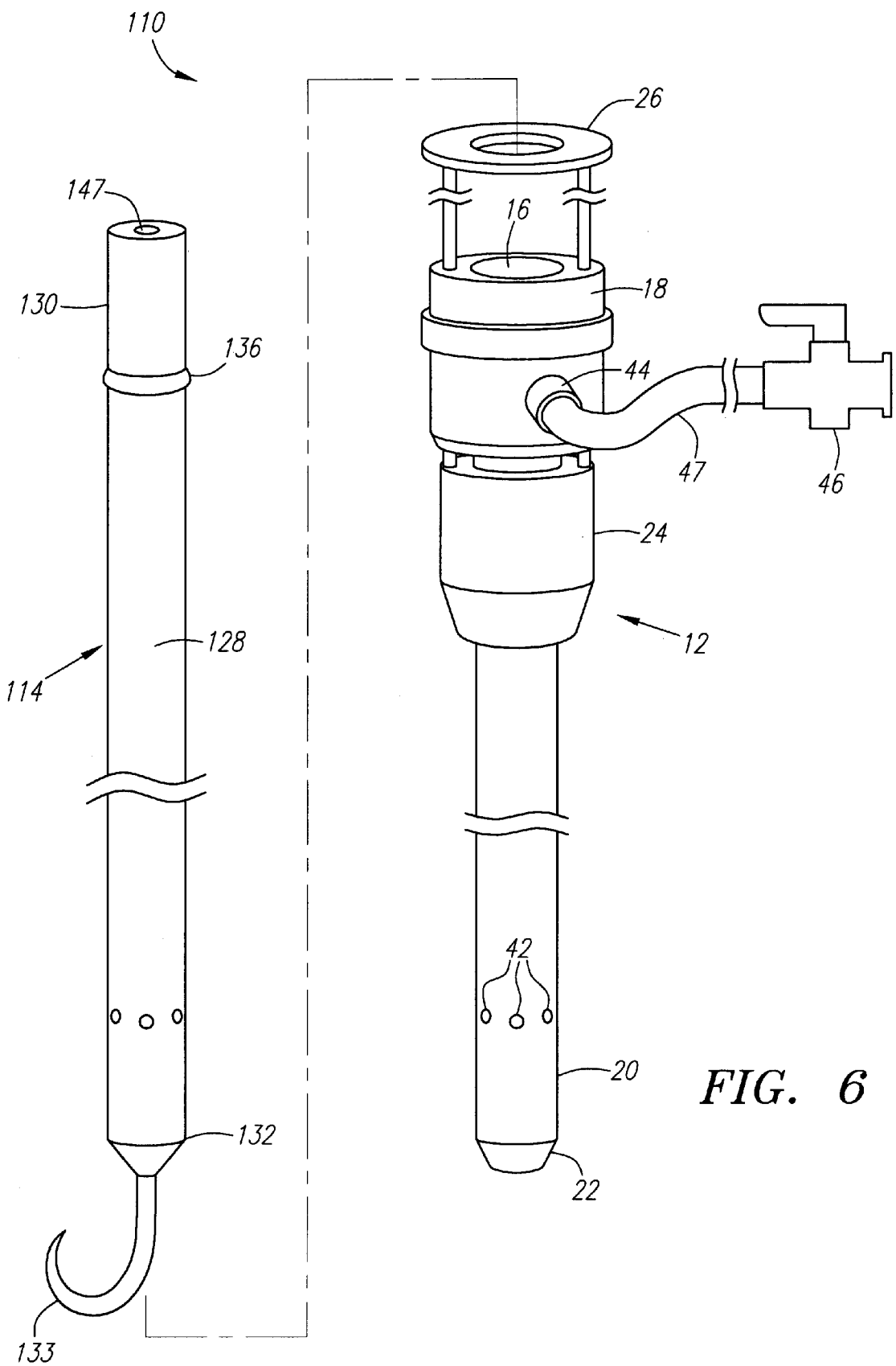
FIG. 6 is a side view of a second preferred embodiment of a vascular sheath and obturator, in accordance with the present invention.

As shown in FIG. 5, the sheath 12 and obturator 14 may then be advanced until the distal side ports 42 enter the blood vessel 90. Internal blood pressure within the blood vessel 90, which is substantially greater than the pressure encountered at the flush port 46, causes blood to enter the distal side ports 42, pass through the annular region 48, and exit the proximal side port 44. The flush port 46 may include substantially transparent tubing 47 such that the blood may be seen or a transparent cannula, chamber or other device may be connected to the flush port 46. Thus, the blood provides a visual indication that the sheath 12 and obturator 14 are properly positioned with respect to the wall 98 of the blood vessel 90.

With the sheath 12 properly positioned, the housing 24 may then be actuated, for example, to advance the housing 24 distally into the incision 92 to deliver the closure element (not shown). Preferably, the housing 24 may only be advanced a predetermined distance such that the closure device substantially engages the wall 98 of the blood vessel around the incision 92, e.g., until the barbs thereon penetrate but do not pass completely through the wall 98. Thus, the distal side ports 42 may be provided a predetermined distance from the distal end 18 of the sheath 12 and the housing 24 may be advanced only a predetermined distance, thereby providing a predetermined distance therebetween that may facilitate proper deployment of the closure element with respect to the wall 98 of the vessel 90.

Figure 7:
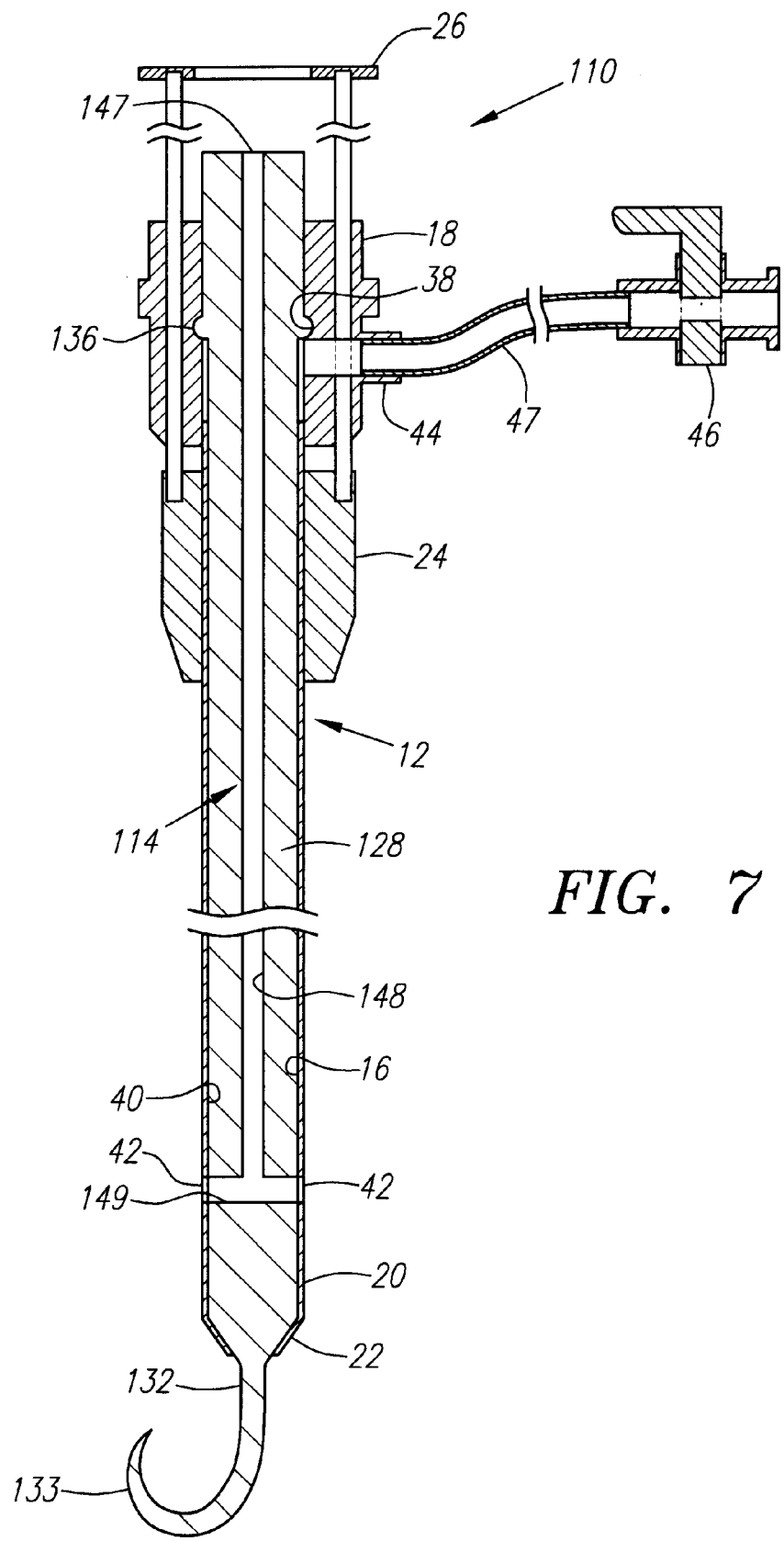
FIG. 7 is a cross-sectional view of the obturator and vascular sheath of FIG. 6, with the obturator fully inserted into the vascular sheath.

Turning to FIGS. 6–9, another preferred embodiment of an apparatus I 10 is shown that includes a sheath 12 that is 'substantially identical to the previous embodiment, and an obturator 114. The obturator 114 is a substantially flexible, or semi-rigid elongate body 128 slidably engageable within a lumen 16 of the sheath 12 and having a proximal end 130 and a distal end 132. An annular ridge 136 is provided on the proximal end 130 that may engage a complementary-shaped pocket 38 or other cooperating detent in the sheath 12 for substantially securing the obturator 114 when it is fully inserted into the sheath 12. The distal end 132 of the obturator 114 may include a substantially flexible pigtail 133 that may facilitate atraumatic advancement into a blood vessel. As best seen in FIG. 7, the obturator 114 also includes a lumen 148 that extends from a proximal outlet 147 to an annular distal recess 149.

Figure 8:
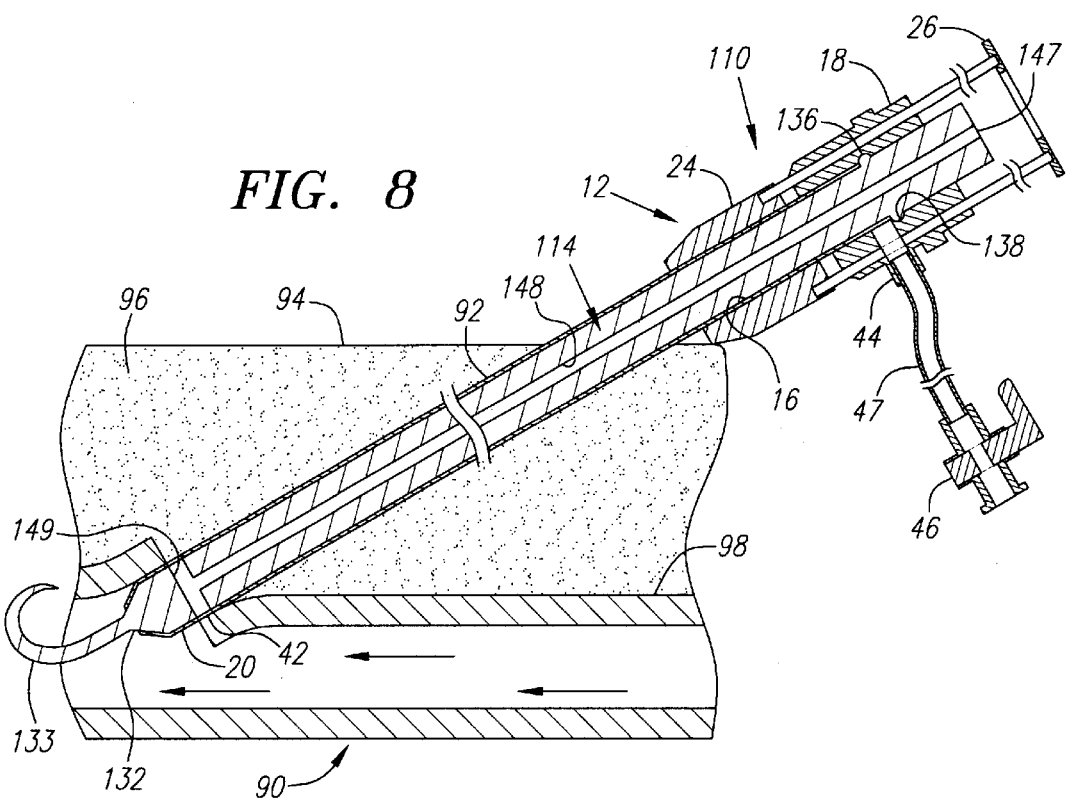
FIG. 8 is a cross-sectional view of the vascular sheath and obturator of FIG. 6 inserted through an incision into a blood vessel, showing side ports in the vascular sheath being disposed outside the blood vessel.

Turning to FIG. 8, the sheath 12 may be positioned within a blood vessel 90 through an incision 92 such that the distal side ports 42 do not communicate with an interior of the vessel 90. After one or more devices (not shown) are inserted through the sheath 12 to perform a desired procedure, the obturator 114 may be inserted into the lumen 16 until the distal end 132 extends beyond the distal end 20 of the sheath 12 and/or the cooperating detents 136, 38 are engaged. Preferably, when the obturator 114 is fully received within the sheath 12, the distal side ports 42 communicate with the annular recess 149. The sheath 12 and obturator 114 may then be moved in conjunction with one another, and preferably are together positioned such that the distal side ports 42 are adjacent to and not within the vessel 90.

Figure 9:
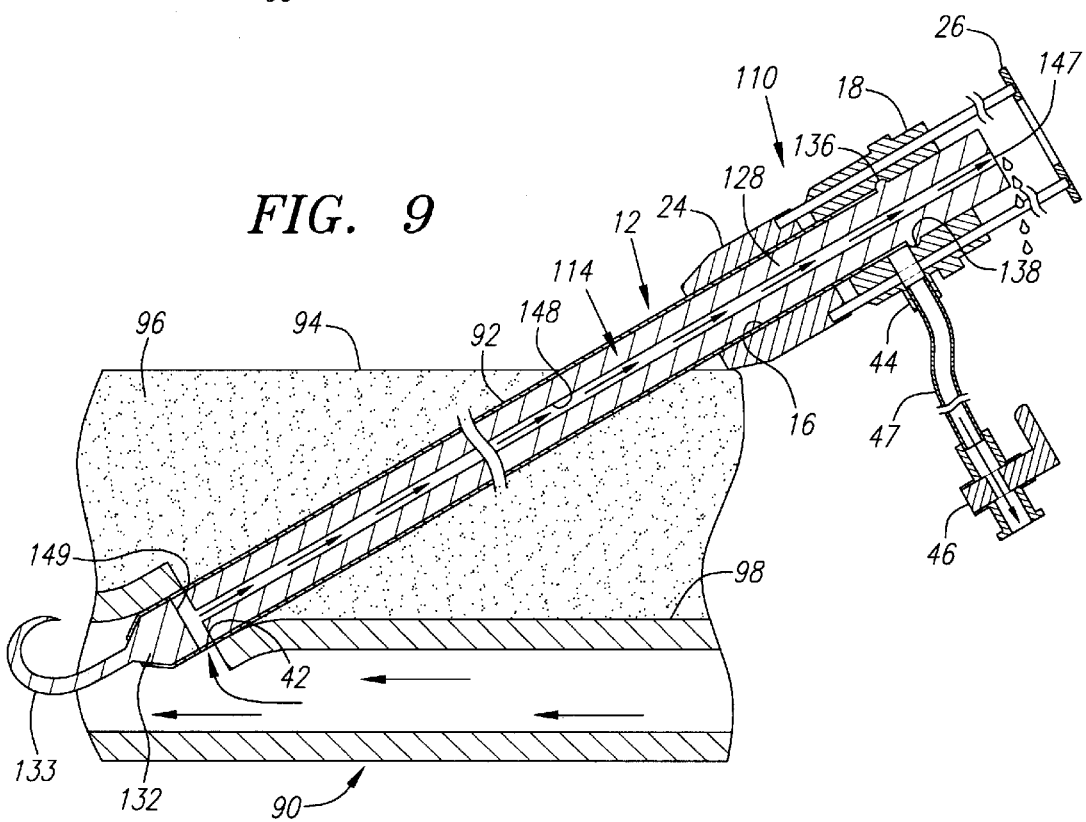
FIG. 9 is a cross-sectional view of the vascular sheath and obturator of FIG. 6 with the sheath advanced such that the side ports are disposed inside the blood vessel.
Figure 10:
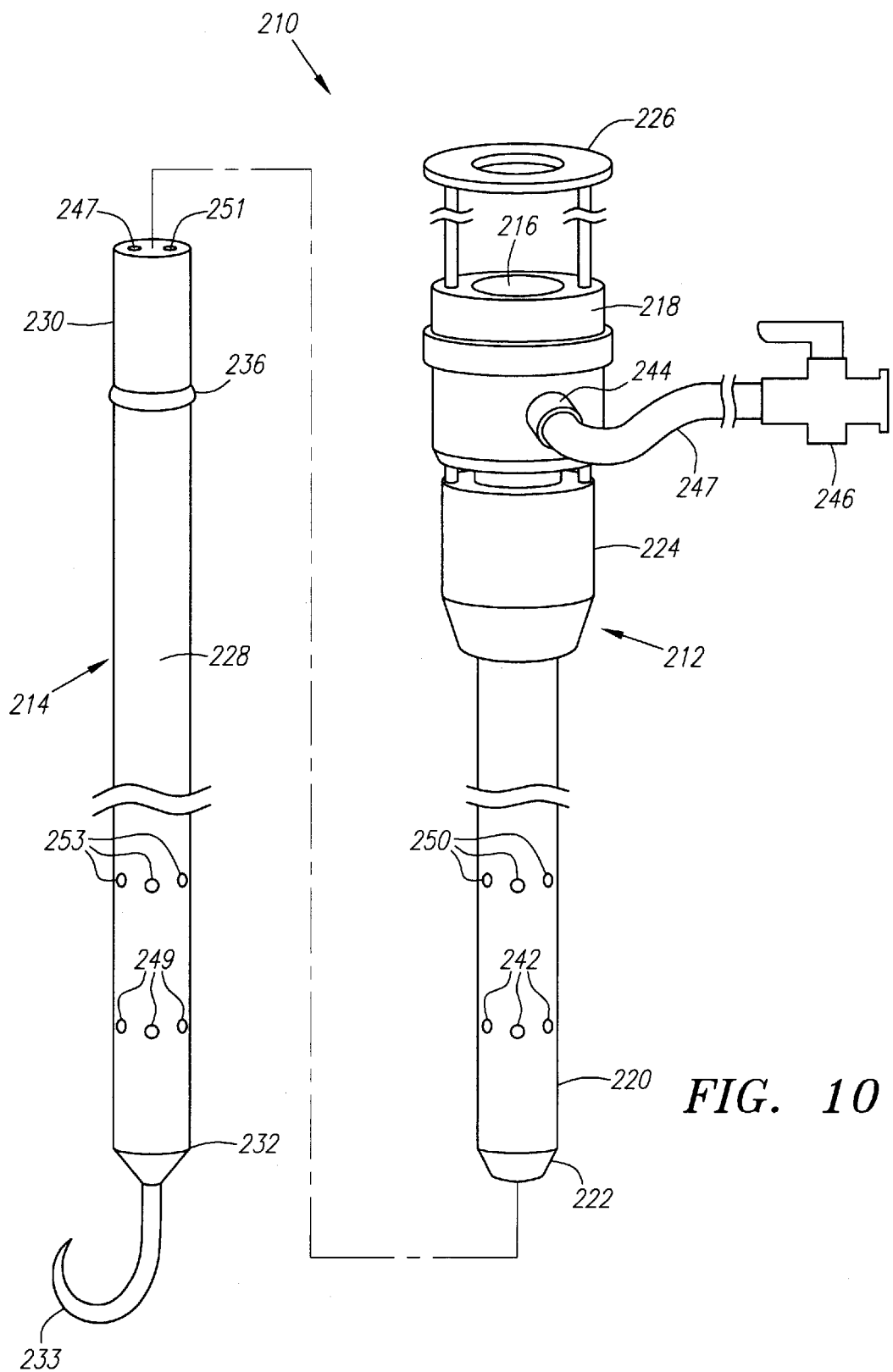
FIG. 10 is a side view of a third preferred embodiment of a vascular sheath and obturator, in accordance with the present invention.
Figure 11:
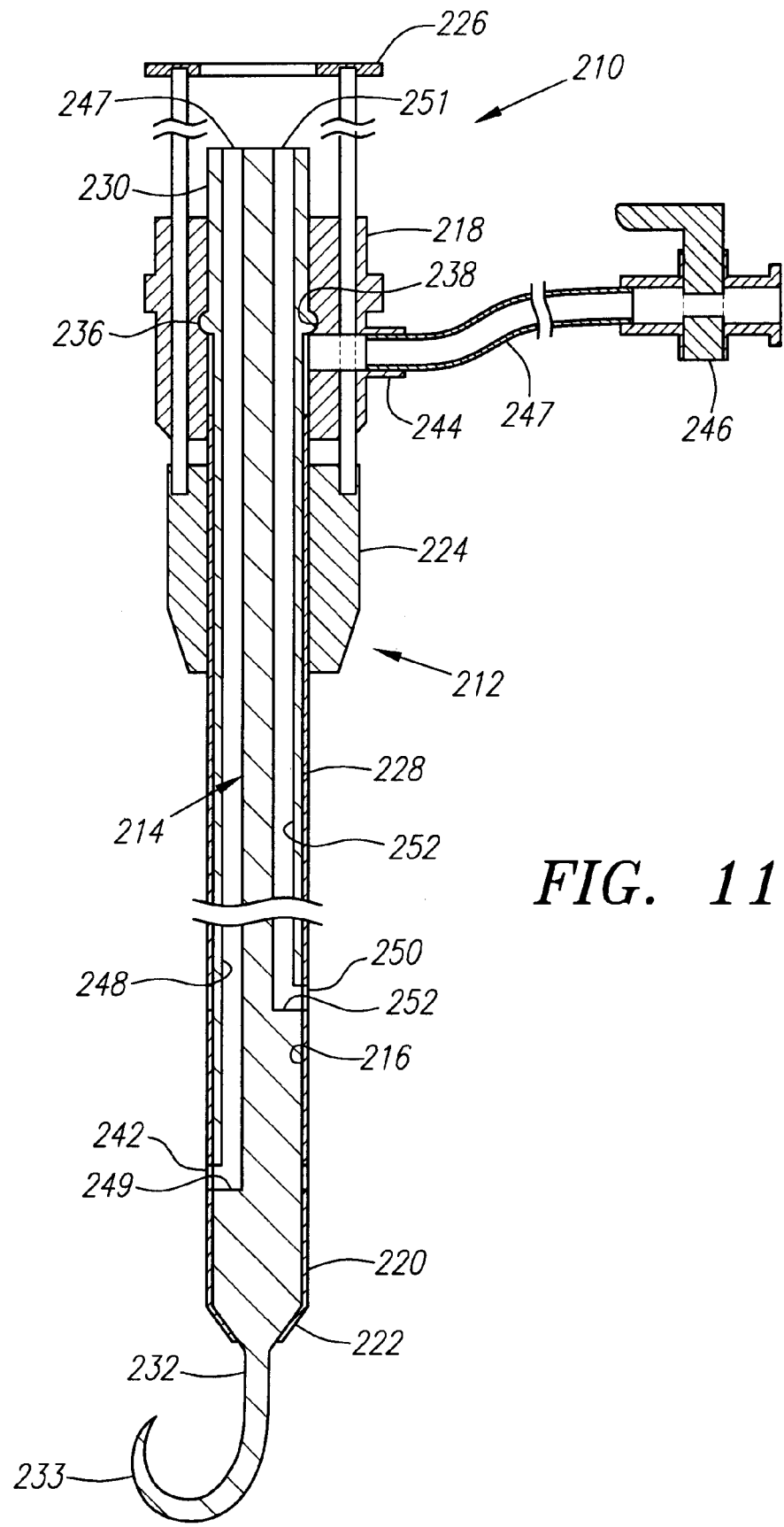
FIG. 11 is a cross-sectional view of the obturator and vascular sheath of FIG. 10, with the obturator fully inserted into the vascular sheath.

As shown in FIG. 9, the sheath 12 and obturator 114 may then be advanced until the distal side ports 42 enter the blood vessel 90. Internal blood pressure within the blood vessel 90 causes blood to enter the distal side ports 42 into the annular recess 149, pass through the lumen 148, and exit the proximal outlet 147. Thus, blood exiting the proximal outlet may provide a visual indication that the sheath 12 and obturator 114 are properly positioned with respect to the wall 98 of the blood vessel 90. The housing 24 may then be actuated to deliver the closure element, as described above.

Turning to FIGS. 10–13, yet another preferred embodiment of an apparatus 210 is shown that includes a sheath 212, and an obturator 214 insertable into the sheath 212. The sheath 212 includes a lumen 216 extending between its proximal and distal ends 218, 220. A housing 224 may be slidably disposed on an exterior of the sheath 212, the housing 224 configured for releasably holding a closure element, as described above (not shown).

The sheath 212 includes first and second sets of side ports 242, 250, each set preferably including a plurality of side ports that communicate with the lumen 216. The distal side ports 242 may be disposed circumferentially about a predetermined location along a length of the sheath 212, e.g., at a predetermined axial location with respect to the housing 224. The sheath 12 may also include a proximal side port 244 at or near the proximal end 218 that also communicates with the lumen 216, to which flush port 246 is connected. The sheath 212 also may include a seal (not shown) within the lumen 216 at or near the proximal end 218 that provides a fluid-tight seal, yet accommodates insertion of the obturator 214 into the lumen 216 without fluid passing proximally from the sheath 212.

The obturator 214 is a substantially flexible, or semi-rigid elongate body 228 having a size for slidably, but sealingly engaging an inner wall 240 of the sheath 212, and including a proximal end 230 and a distal end 232. An annular ridge 236 is provided on the proximal end 230 that may engage a complementary-shaped pocket 238 in the sheath 212 for substantially securing the obturator 214 within the sheath 212, similar to the embodiments described above. The distal end 232 of the obturator 214 my also be substantially soft and/or flexible, possibly including a pigtail (not shown), to facilitate atraumatic advancement into a blood vessel.

The obturator 214 includes first and second lumens 248, 252 that include first and second sets of distal openings 249, 253 and proximal openings 247, 251. Preferably, when the obturator 214 is fully received in the sheath 212, e.g., when the cooperating detents 236, 238 engage one another, the first and second sets of distal openings 249, 253 are axially aligned with the first and second sets of side ports 242, 250, respectively. The obturator 214 may be rotatable within the sheath 212 to further line the openings 249, 253 and side ports 242, 250 such that the first and second sets of side ports 242, 250 may communicate with the lumens 248, 252, respectively.

Figure 12:
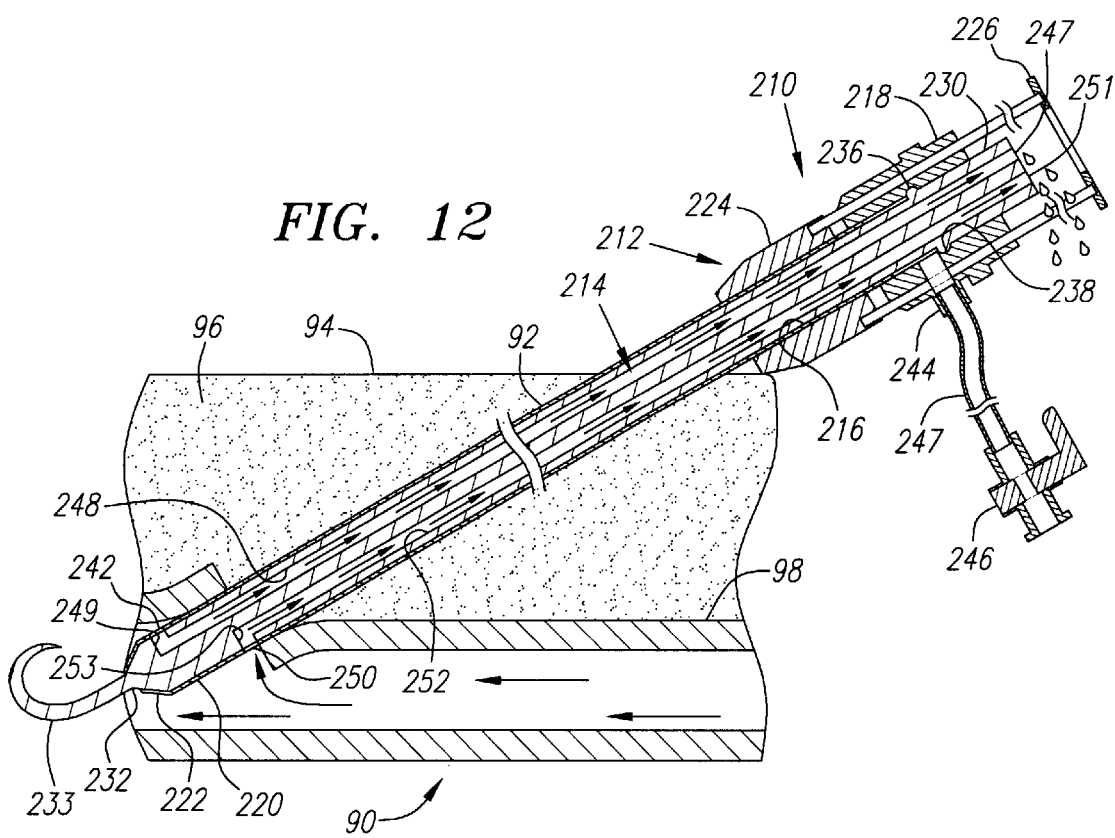
FIGS. 12 and 13 are cross-sectional views of the vascular sheath and obturator of FIG. 10 with the sheath advanced such that first and second backbleed ports in the vascular sheath are disposed within the blood vessel, and only first backbleed ports in the vascular sheath are disposed within the blood vessel, respectively.
Figure 13:
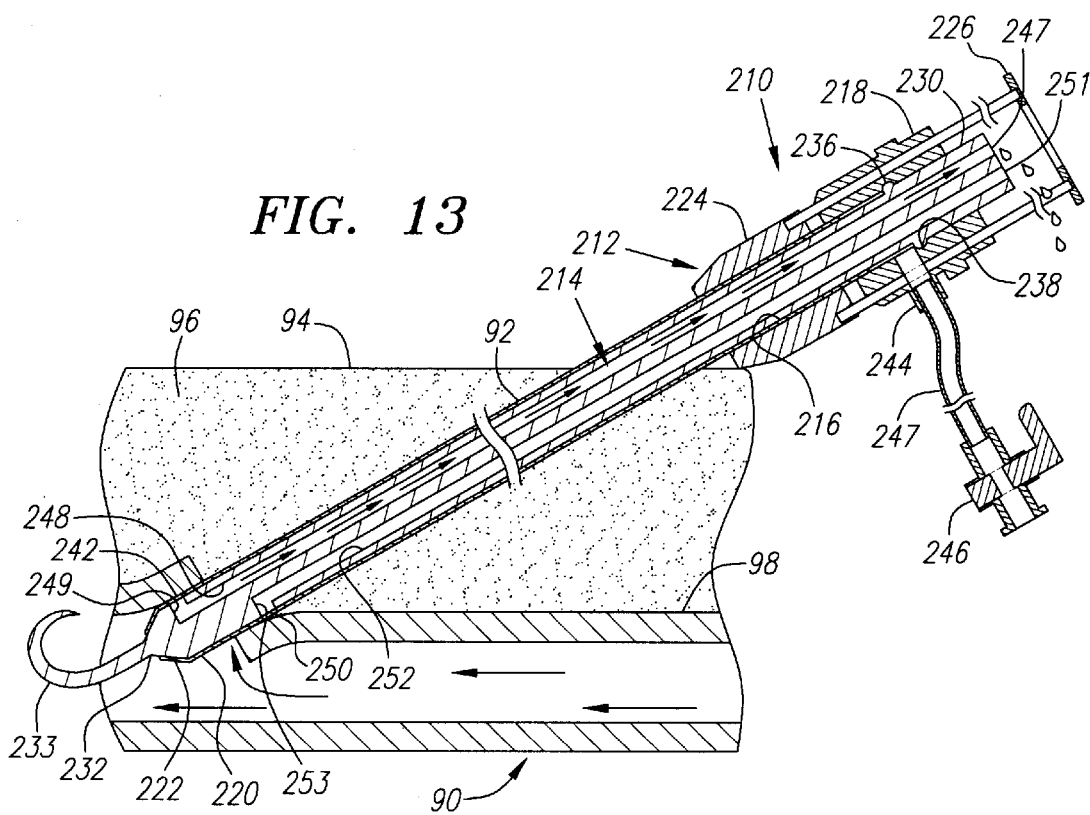

As best seen in FIGS. 12 and 13, during use of the apparatus 210, the sheath 212 may be disposed within a blood vessel 90 through an incision 92. After a procedure is completed using instruments introduced through the sheath 212, the obturator 214 may be inserted into the lumen 216 until the cooperating detents 236, 238 are engaged. If necessary, the obturator 214 may be rotated to align the first and second sets of side ports 242, 250 with the first and second sets of openings 249, 253, respectively. Alternatively, mating notches (not shown) may be provided, for example, on the cooperating detents 236, 238, that ensure that the obturator 214 and sheath 212 are rotatably aligned with one another.

The sheath 212 and obturator 214 may then be moved axially together into or out of the vessel 90. As shown in FIG. 12, in one position, both sets of side ports 242, 250 are exposed within the vessel 90, and the blood pressure therein, whereupon both proximal outlets 247, 251 may provide a "backbleed" visual indication. Alternatively, as shown in FIG. 13, only the distal or first set of side ports 242 may be exposed within the vessel 90, and provide a visual indication that the sheath 212 is not inserted as far as into the vessel 90 as in FIG. 12. In a further alternative, neither set of side ports 242, 250 may be provide a visual indication, indicating that the sheath 212 is withdrawn further or perhaps completely from the vessel 90. Thus, a plurality of side ports at different axial positions along the sheath 212 may be used as a depth gauge, providing the user a visual indication that the sheath 212 is at one of a plurality of known locations or depths with respect to the vessel 90.

With the sheath 212 inserted a desired depth, the housing 224 may then be actuated to deliver the closure element (not shown). Alternatively, the housing and closure element may be eliminated, and the sheath 212 and obturator 214 may be used as an introducer device having a depth gauge indicator, as will be appreciated by those skilled in the art.

Figure 14A:
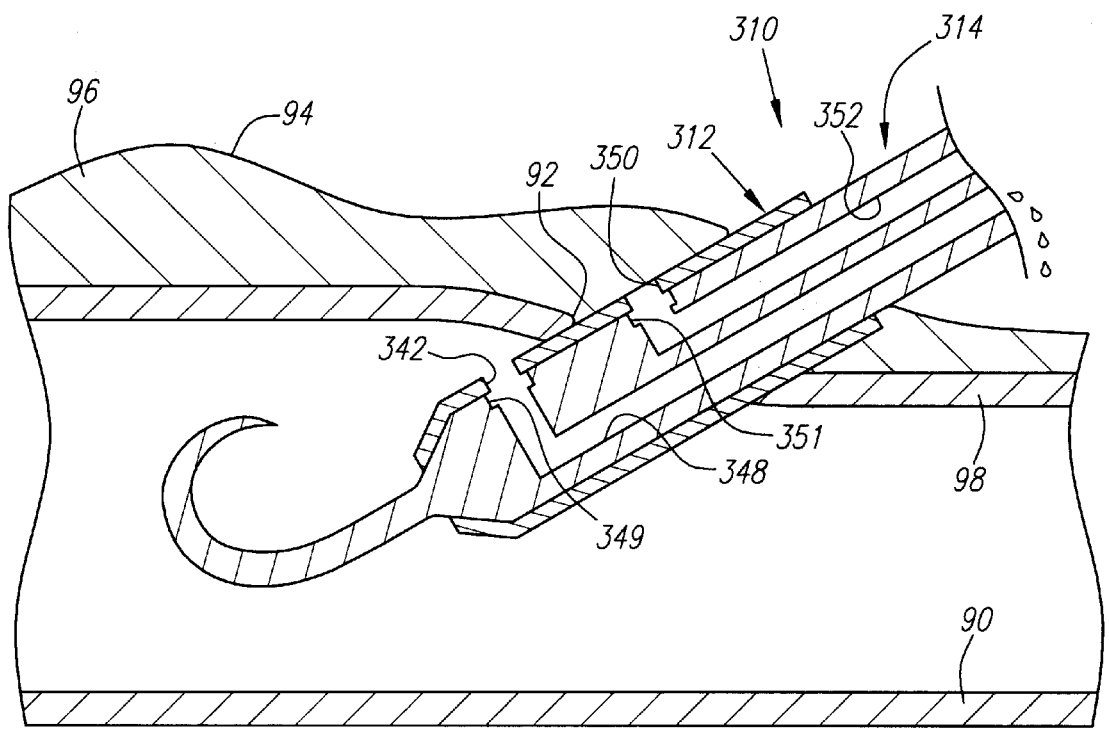
FIGS. 14A and 14B are cross-sectional views of a blood vessel, showing another preferred embodiment of a vascular sheath and obturator, including a pair of axially aligned backbleed ports in the vascular sheath.
Figure 14B:
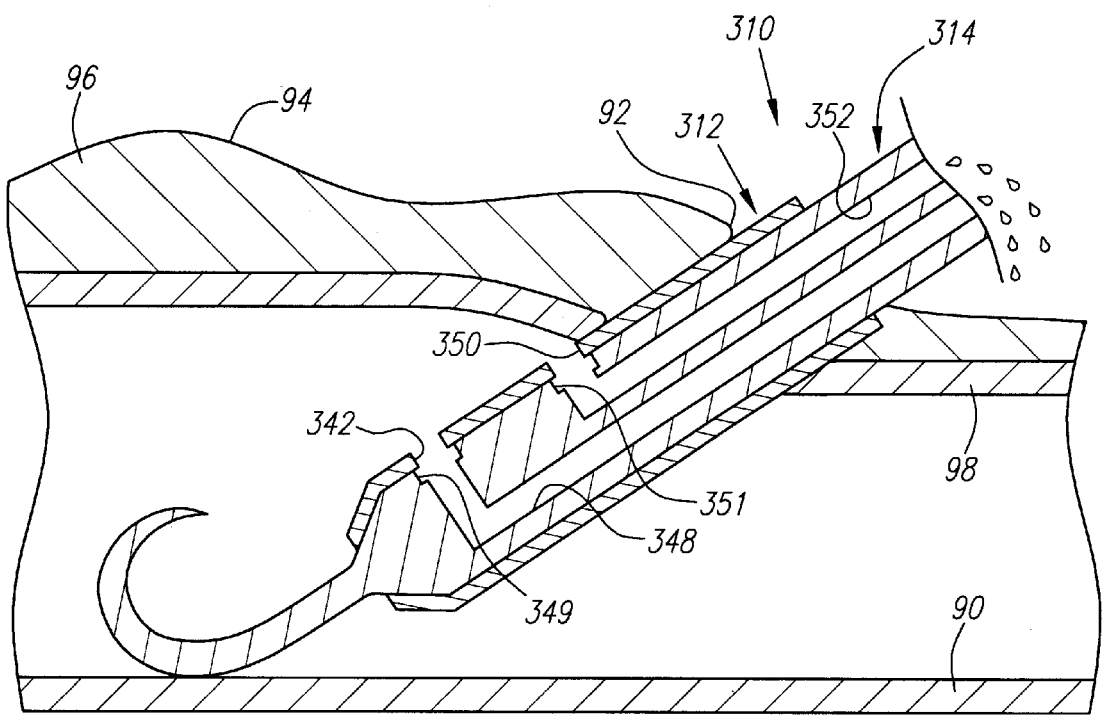

Turning to FIGS. 14A and 14B, still another preferred embodiment of an apparatus 310 is shown that includes a sheath 312 and obturator 314 similar to the previous embodiment. Unlike the previous embodiment, however, the sheath 312 includes first side port 342 and a second side port 350 instead of a plurality of side ports in each set. The first and second side ports 342, 350 are axially aligned with one another, i.e., at a similar peripheral location about the exterior of the sheath 312. The obturator 314 includes first and second annular recesses 349, 351 that are spaced apart axially a distance similar to the distance between the first and second side ports 342, 350. Thus, when the obturator 314 is fully inserted into the sheath 312, the first and second side ports 342, 350 are substantially aligned with the first and second annular recesses 349, 351, respectively, such that the first and second side ports 342, 250 communicate with first and second lumens 348, 352 within the obturator 314. In an alternative embodiment, the obturator may include a first lumen that may communicate with the first side port, and the obturator may include a reduced diameter region, similar to the embodiment shown in FIGS. 1 and 2, such that the second side port may communicate with the annular region defined between the sheath and the obturator.

The apparatus 310 preferably includes a visible marker (not shown), for example, on the proximal end (not shown) of the sheath 312 at a predetermined peripheral location. For example, the marker may be axially aligned with the first and second side ports 342, 350 to thereby provide a visual indication of the peripheral location of the side ports 342, 350. The apparatus 310 may then be used similar to the embodiments described above to position the sheath 312 within a blood vessel 90 and/or to deliver a closure element to close an incision 92 communicating with the vessel 90. During this procedure, the marker may be used to orient the sheath 312, for example, to rotate the side ports 342, 350 into an "anterior" orientation, i.e., towards the outer surface of the patient's skin 94. This may provide more precise control of the depth of the sheath, e.g., by taking into account the fact that the sheath 312 is inserted at an angle into the blood vessel 90, as will be appreciated by those skilled in the art.

Turning to FIGS. 15A and 15B, yet another embodiment of an apparatus 410 is shown that includes a sheath 412, and an obturator 414, similar to the previous embodiments. The apparatus 410 optionally may include a clip housing, clip, actuator handle and the like (not shown), e.g., on the sheath 412, similar to the previous embodiments. The sheath 412 includes first side port 442 and a second side port 450. The first and second side ports 442, 450 may be axially aligned with one another, i.e., at a similar peripheral location about the exterior of the sheath 412, or they may be offset from one another about the periphery. The obturator 414 includes an enlarged distal region 432, and a relatively narrow region 428 extending between the distal region 432 and a proximal end 430 of the obturator 414.

A protrusion 429, which may be a partial annulus or a hub, extends radially outward from the narrow region 428 to slidably engage an inner wall 440 of the sheath 412. The protrusion 429 is located a predetermined distance from the distal region 432 such that the protrusion 429 may selectively open or close the first and seconds side ports 442, 450. When the obturator 414 is inserted a first distance into the sheath 412, as shown in FIG. 15A, the protrusion 429 may sealably obstruct the second side port 450, thereby allowing fluid to enter the first side port 442 and pass through an annular lumen 448 to a proximal side port 444. The obturator 414 and sheath 412 may include cooperating detents, e.g., annular ridge 436 and a first annular groove 438a, for releasably securing the obturator 414 in the first position shown in FIG. 15A.

As shown in FIG. 15B, the obturator 414 may be advanced distally to a second position at which the protrusion 429 sealably obstructs the first side port 442, thereby allowing fluid to enter the second side port 450. The sheath 412 may include a second annular groove 438b for receiving the ridge 436 on the obturator 414 for releasably securing the obturator 414 in the second position.

During a procedure, the apparatus 410 may be used similar to the embodiments described above to position the sheath 412 within a blood vessel and/or to deliver a closure element to close an incision communicating with the vessel. First, the sheath 412 may be manipulated, e.g., advanced further into the vessel or retracted partially from the vessel, until the first and second side ports 442, 450 are positioned outside the vessel, i.e., within the puncture passage. A marker (not shown) may be used to orient the sheath 412, for example, to rotate the side ports 442, 450 into an "anterior" orientation, as described above. The obturator 414 may be inserted into the sheath 412 until it reaches the first position. The sheath 412 and obturator 414 may then be manipulated together, i.e., advanced or retracted, until internal blood pressure directs blood through the first side port 442 and into the proximal side port 444, indicating that the first side port 442 is within the vessel. The obturator 414 may then be advanced to the second position, occluding the first side port 442. The sheath 412 and obturator 414 may then be manipulated until blood enters the second side port 450 and exits the proximal side port 444, indicating the precise depth of the sheath 412.

Turning to FIGS. 16A and 16B, still another embodiment of an apparatus 510 is shown that includes a sheath 512, including first side port 542 and a second side port 550, and an obturator 514. The sheath 512 optionally may include a clip housing, clip, actuator handle and the like (not shown), similar to the previous embodiments. The first and second side ports 542, 550 may be axially aligned with one another, i.e., at a similar peripheral location about the exterior of the sheath 512, or they may be offset from one another about the periphery. The obturator 514 includes an enlarged distal region 532, and a relatively narrow region 528 extending between the distal region 532 and a proximal end 530 of the obturator 514.

An annular piston 529 extends radially outward from the narrow region 528 to slidably engage an inner wall 540 of the sheath 512, thereby sealing a region distal of the piston 529, i.e., between the piston 529 and the enlarged distal region 532. The piston 529 is located a predetermined distance from the distal region 528 such that the piston 529 may selectively open or close the first and seconds side ports 542, 550. The obturator 514 also includes a lumen 552 that extends from a proximal outlet 553 to a distal inlet 551 located distally of the piston 529.

When the obturator 514 is inserted a first distance into the sheath 512, as shown in FIG. 16A, the piston 529 may sealably obstruct the second side port 550, thereby allowing fluid to enter the first side port 542 and pass through the obturator lumen 552 to the proximal outlet 553. The obturator 514 and sheath 512 may include cooperating detents, e.g., annular ridge 536 and a first annular groove 538a, for releasably securing the obturator 514 in the first position shown in FIG. 16A.

As shown in FIG. 16B, the obturator 514 may be advanced distally to a second position at which the piston 529 sealably obstructs the first side port 550, thereby allowing fluid to enter the second side port 542 and pass through the annular lumen 548 to proximal side port 544. The sheath 512 may include a second annular groove 538b for receiving the ridge 536 on the obturator 514 for releasably securing the obturator 514 in the second position.

The apparatus 510 may be used similar to the embodiments described above to position the sheath 512 within a blood vessel and/or to deliver a closure element to close an incision communicating with the vessel. A marker (not shown) may be used to orient the sheath 512, for example, to rotate the side ports 542, 550 into an "anterior" orientation, as described above. The obturator 514 may be inserted into the sheath 512 until it reaches the first position. The sheath 512 and obturator 514 may then be manipulated, i.e., advanced or retracted, until internal blood pressure directs blood through the first side port 542 and into the proximal side port 544, indicating that the first side port 542 is within the vessel. The obturator 514 may then be advanced to the second position, occluding the first side port 550. The sheath 512 and obturator 514 may then be manipulated until blood enters the second side port 542 and exits the proximal side port 544, indicating the precise depth of the sheath 512.

Turning to FIGS. 17A–17H, yet another alternative embodiment is shown of an apparatus 610, including a sheath 612, including first and second side ports 642, 650, and an obturator 614. The sheath 612 optionally may include a clip housing, clip, actuator handle and the like (not shown), similar to the previous embodiments. The first and second side ports 642, 650 may be axially aligned with one another, i.e., at a similar peripheral location about the exterior of the sheath 612, as shown or they may be offset from one another about the periphery (not shown). The obturator 614 includes an enlarged distal region 632 that slidably and sealingly engages an inner wall 640 of the sheath 612. The obturator 614 also includes a relatively narrow region 628 extending between the distal region 632 and a proximal end 630 of the obturator 514, thereby defining an annular lumen 648 between the narrow region 628 and an inner wall 640 of the sheath 612.

A notch or slot 629 is provided in the distal region 632 of the obturator 614 that communicates with the lumen 648. The obturator 514 also includes a lumen 652 that extends from a proximal outlet 653 to a distal inlet 651 located distally of the notch 629. Preferably, the outlet 651 and the notch 629 are aligned with the first and second side ports 642, 650 when the obturator 614 is fully inserted into sheath 612.

The obturator 614 is rotatable within the sheath 612 between first and second positions. As best seen in FIGS. 17A and 17E, in the first position, the outlet 651 communicates with the first side port 642, while the second side port 650 is substantially sealed by the enlarged distal portion 632 of the obturator 614. Thus, fluid may enter the first side port 642 and pass through the obturator lumen 652 to the proximal outlet 653. The obturator 614 and sheath 612 may include cooperating detents 636, 638a for releasably securing the obturator 614 in the first position, as best seen in FIG. 17C.

As best seen in FIGS. 17B and 17G, the obturator 614 may be rotated to the second position such that the enlarged distal region 632 of the obturator 614 sealably obstructs the first side port 650, while fluid may freely enter the second side port 642 and pass through the notch 629 into the annular lumen 648 to proximal side port 644. The sheath 612 may include a second detent 638b for engaging the detent 636 on the obturator 614 for releasably securing the obturator 614 in the second position.

The apparatus 510 may be used similar to the embodiments described above to position the sheath 512 within a blood vessel and/or to deliver a closure element to close an incision communicating with the vessel, except that the obturator 614 is rotated within the sheath 612 rather than moved axially in order to selectively open or close the first and second side ports 642, 650. In an alternative embodiment, the obturator 614 may include two lumens (not shown), one that may selectively communicate with the respective first and second side ports 642, 650 when the obturator 614 is rotated within the sheath 612, as will be appreciated by those skilled in the art.

Figure 18:
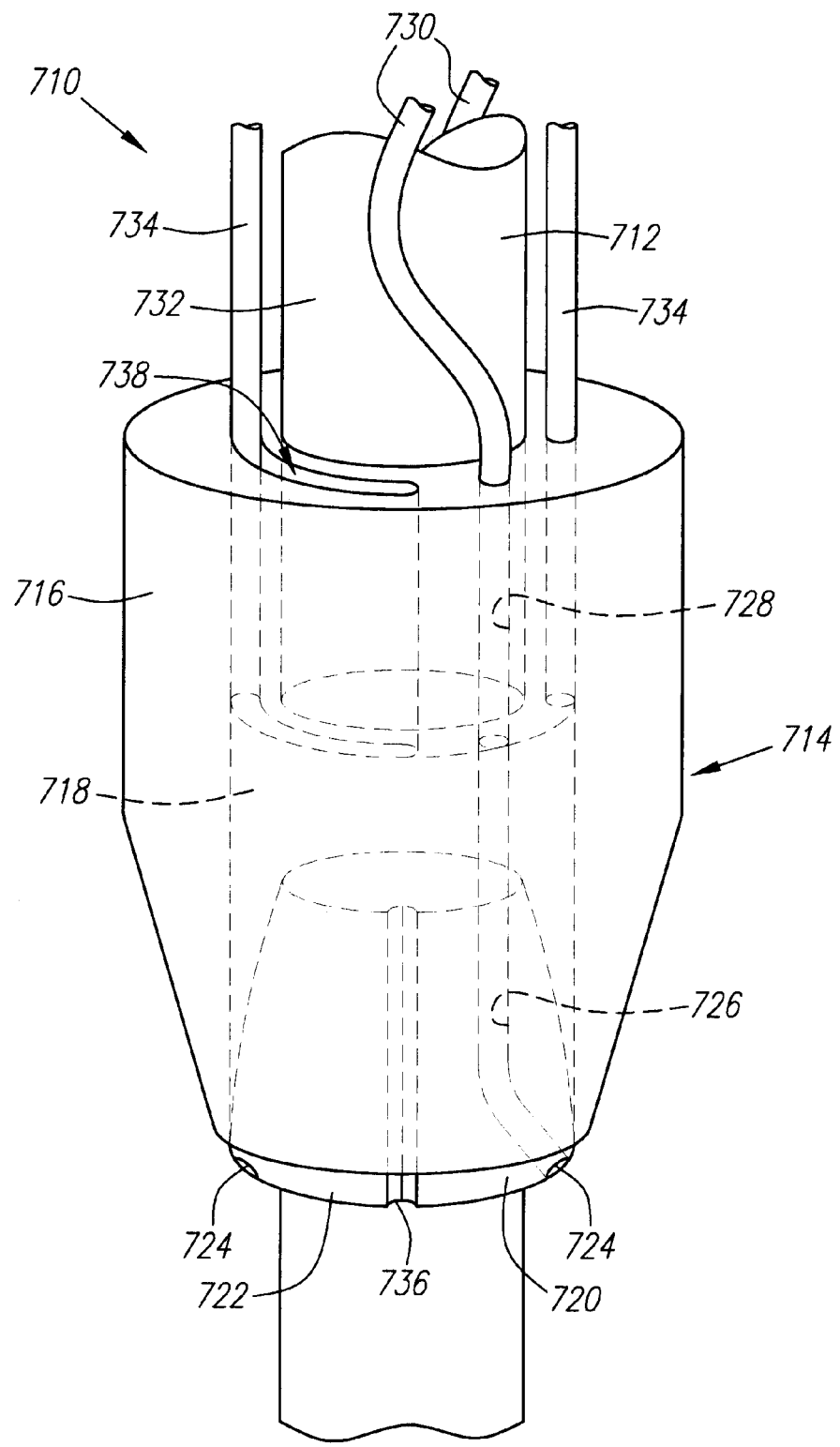
FIG. 18 is a detail of a clip housing on an introducer sheath, in accordance with the present invention.

Turning to FIG. 18, another embodiment of the present invention is shown, namely an apparatus 710 that includes a sheath or introducer 712, and a clip housing 714. The clip housing 714 includes an outer member 716 defining an annular cavity 718, and an inner member 720 that is partially receivable in the cavity 718. The inner member 720 includes a tapered distal end 722 within which are one or more ports 724. The ports communicate through a lumen 726 within the inner member 720 to a lumen 728 within the outer member 716 and to tubes 730. The clip housing 714 is slidable along an outer surface 732 of the sheath 712, and may be actuable, for example, using handle rods 734.

With the outer and inner members 716, 720 separated from one another, a clip or other closure device (not shown) may be placed within the cavity 718. For example, the inner member 720 may be removed distally from the sheath 712, and a clip may be advanced over the distal end (not shown) of the sheath 712 and into the cavity 718. The inner member 720 may then be advanced over the distal end of the sheath 712 until it partially enters the cavity 716, i.e., substantially engages the outer member 716. For example, the inner and outer members 720, 716 may include a cooperating groove 736 and notch (not shown) that may facilitate alignment and/or engagement of the inner and outer members 720, 716.

The sheath 712, with the clip housing 714 adjacent a proximal end thereof (not shown) may be placed through a puncture into a blood vessel, for example, until the distal end of the sheath 712 is disposed within the vessel lumen (not shown). A procedure may be completed, e.g., by introducing one or more instruments or other devices through the sheath 712 into the vessel. Upon completion of the procedure, the clip housing 714 may be advanced towards the distal end of the sheath 712, i.e., through the puncture until the clip housing just enters the vessel. The tapered end 722 of the inner member 720 may facilitate substantially atraumatic advancement of the clip housing 714 through the puncture with minimal harm to the surrounding tissue.

As the tapered end 722 enters the vessel, the ports 724 may communicate with the lumen, thereby causing blood to enter the ports, travel through the lumens 726, 728 and the tubes 730, thereby providing an indicator that the clip housing 714 has been properly positioned within the puncture. The clip housing 714 may then be activated, e.g., by rotating the rods 734 within slots 738, to deploy the clip. The sheath 712 may then be withdrawn from the vessel and. puncture site, leaving the clip in the puncture site to substantially close the puncture opening into the vessel.

Figure 19A:
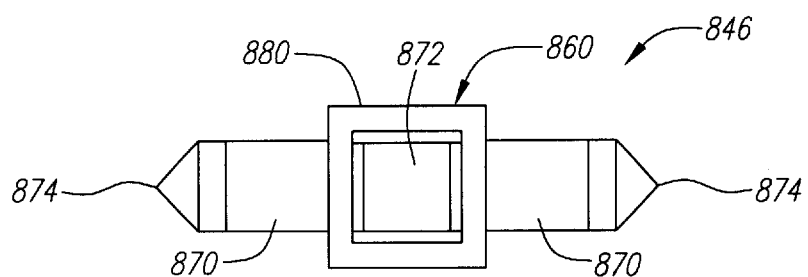
FIGS. 19A–19C are, respectively, views of a bioabsorbable clip and fastener of the present invention shown in top view in a delivery configuration, in side view in the delivery configuration. and in side view in a deployed configuration.
Figure 19B:
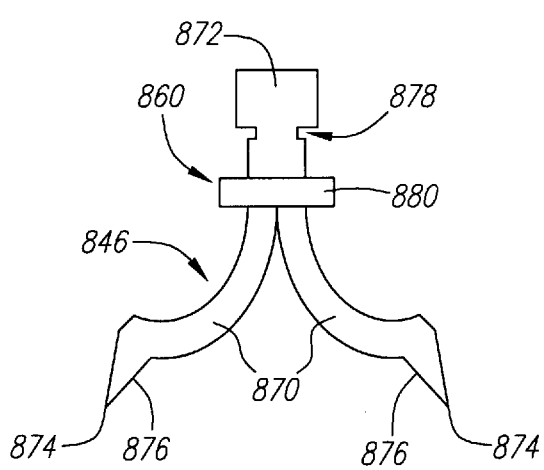
Figure 19C:
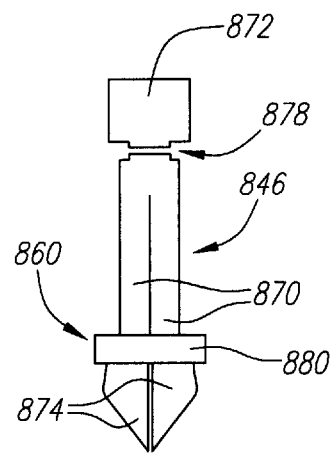

With reference now to FIGS. 19A–19C, bioabsorbable clip 846 and fastener 860 are described in greater detail. FIG. 19A shows clip 846 in the delivery configuration. Clip 846 comprises curved legs 870 and proximal end 872. Legs 870 distally terminate at spikes 874 with optional engagement means 876, and proximally terminate at narrowed region 878. Engagement means 876 may comprise, for example, barbs or hooks.

Fastener 860 comprises bioabsorbable locking collar 880, which is slidably received on the exterior of clip 846. As seen in FIG. 19B, locking collar 880 may be distally advanced down the exterior of clip 846 to deform the clip to its deployed configuration. wherein curved legs 870 and spikes 874 are drawn together. Clip 846 may then be separated from clip holder 856 by rotating proximal end 872 with respect to legs 870. causing the clip to snap into two pieces at narrowed region 878, for the reasons described hereinafter. Clip 846 and locking collar 880 preferably are fabricated from bioabsorbable materials, such as polyglycolic acid.

Figure 20A:
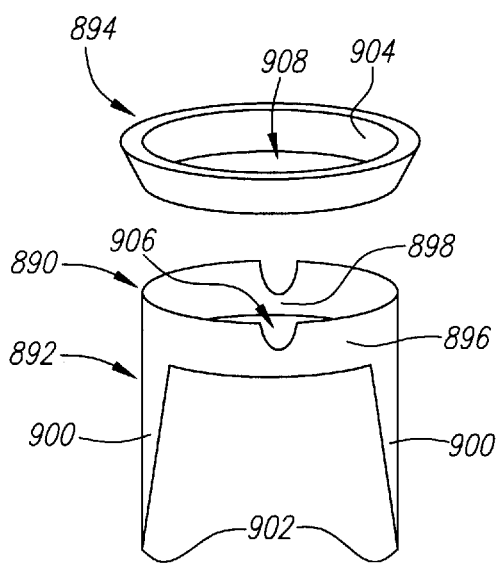
FIGS. 20A and 20B are isometric views of an alternative embodiment of the bioabsorbable surgical clip and fastener, constructed in accordance with the present invention and shown, respectively, in a delivery configuration and in a deployed configuration.
Figure 20B:
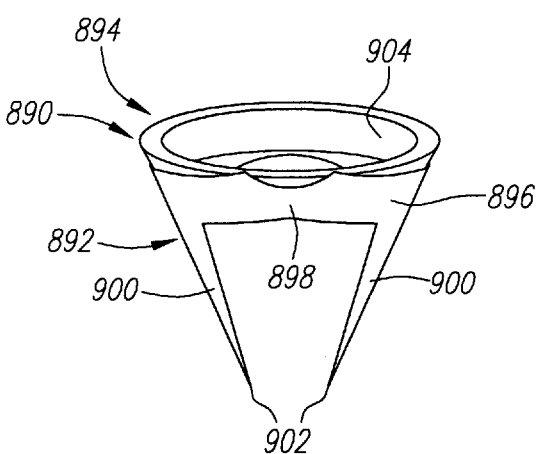

Referring to FIG. 20, an alternative embodiment of the closure component of the present invention is described. Closure component 890 comprises bioabsorbable clip 892 and fastener 894. Clip 892 comprises proximal hoop 896 with narrowed regions 898, and legs 900 terminating in spikes 902. Fastener 894 comprises bioabsorbable wedge 904. Wedge 904 has a diameter substantially equal to the diameter of hoop 896 at its distal end, the diameter tapering to a maximum diameter at the proximal end of wedge 904. Clip 892 therefore may be deformed from the delivery configuration of FIG. 20A to the deployed configuration of FIG. 20B, wherein legs 900 and spikes 902 are drawn together, by advancing wedge 904 into hoop 896 to deform clip 892 at narrowed regions 898. Lumen 906 extends through hoop 898 of clip 892, while lumen 908 extends through wedge 896. Clip 892 and wedge 896 therefore are configured for delivery over the exterior of an introducer sheath. The clip and wedge preferably are fabricated from bioabsorbable materials.

With reference to FIGS. 21A–21B through 24A–24B, in conjunction with FIGS. 1–3. methods of using vascular device 10 are described. Introducer sheath 12 is advanced through skin, fat, and muscle tissue into vessel V, through vascular puncture P, which is formed in accordance with well-known techniques. Vascular device 10 is used in the same manner as a standard introducer sheath.

As shown in FIG. 21A, distal pins 850. mounted in housing 816, abut distal slots 866 and 868 of drivers 858 and holders 856. respectively.

FIG. 21B illustrates closure component 820 via sectional views. FIG. 21A shows the locations of proximal pins 854 within proximal slots 862 and 864, and the locations of distal pins 850 within distal slots 866 and 868, corresponding to the relative longitudinal positions of clip holders 856 and locking collar drivers 858 depicted in FIG. 21B. Pin locations are shown via side views of clip holders 856 and locking collar drivers 858 at the relevant locations.

As seen in FIGS. 21A and 21B, with clip housing 816 positioned at puncture site P. proximal pins 854, mounted in caps 852. are positioned at the extreme right of proximal driver slots 862 and of the circumferential portions of proximal holder slots 864. Distal pins 850 are located at the distal end of distal driver slots 866 and of the longitudinal portions of distal holder slots 868.

In FIGS. 22A and 22B, with clip housing 816 held immobile, force is applied to caps 852 to distally advance clips 846 with respect to housing 816. Specifically, proximal pins 854 abut and apply force against proximal slots 862 and 864, which advances drivers 858 and clip holders 856, as well as attached clips 846 and locking collars 880. Distal pins 850 move freely within distal slots 866 and the longitudinal portions of distal slots 868. Distal advancement of clips 846 continues until pins 850 abut against the proximal end of the longitudinal portions of distal holder slots 868 of clip holders 856. Drivers 858 likewise are restrained by their connection to clip holders 856 via proximal pins 854. The tissue-engaging members, spikes 874 and engagement means 876, of clips 846 contact and pierce the wall of vessel V on opposite sides of the puncture site P.

As seen in FIGS. 23A and 23B, once the spikes have pierced the vessel wall, locking collar drivers 858 are advanced distally while clip housing 816 and clip holders 856 remain stationary, thereby distally advancing locking collars 880 down the exteriors of clips 846 to draw legs 870 and spikes 874 together to close puncture P. Engagement means 876 serve to retain the clips within the vessel wall during healing.

To achieve this advancement of drivers 858 with respect to clip holders 856, caps 852 are rotated clockwise, as viewed from above. until proximal pins 854 abut against the extreme left of proximal slots 862 and 864, thereby aligning the pins with the longitudinal portions of proximal holder slots 864. Then, force is once again applied to caps 852 to advance drivers 858 and deform clips 846 to their deployed configurations. Specifically. proximal pins 854 abut and apply force to proximal driver slots 862, thereby distally advancing drivers 858. Pins 854 move freely within the longitudinal portions of proximal holder slots 864 until they abut against the distal ends of slots 864. Likewise, distal driver slots 866 move freely until distal pins 850 abut the proximal ends of slots 866. In FIG. 23A, when proximal pins 854 abut slots 864 and distal pins 850 abut slots 866, locking collars 880 have been driven down the exteriors of clips 846, thereby deforming the clips to draw legs 870 together and close the puncture site.

In FIGS. 24A and 24B, with clips 846 deformed to seal puncture P. clip holders 856 are detached from clips 846 by snapping the clips free at narrowed regions 878. At this point, or prior to detachment, a suitable biocompatible bioglue or tissue sealant optionally may be injected into the puncture tract, as discussed hereinabove, through device port 832 or side port 822, to aid in sealing vascular puncture P. Alternatively. the bioglue or tissue sealant may be delivered through the backbleed path described above. Vascular device 10 then is withdrawn from the vessel wall, completing the procedure.

Clips 846 are detached from clip holders 856 by rotating caps 852 counterclockwise, as viewed from above. Proximal pins 854 of caps 852 move freely within proximal driver slots 862, but abut against the distal end of the longitudinal portions of proximal holder slots 864 and cause clip holders 856 to rotate with respect to collar drivers 858. Distal pins 850 of clip housing 816 move freely within the circumferential portions of distal holder slots 868 during rotation of clip holders 856. Meanwhile, drivers 858 are restrained from rotation by distal pins 850, which abut against distal driver slots 866. Bioabsorbable clips 846 do not rotate because the square cross section of square clip bores 847 of drivers 858 matches the substantially square cross section of clips 846. thus, since drivers 858 are restrained from rotation, so are clips 846. Non-square cross sections for clips 846 and bores 847, capable of performing the restraining function, will be apparent to those of skill in the art and fall within the scope of the present invention.

Since clips 846 are restrained while clip holders 856 rotate, and since proximal ends 872 of clips 846 are attached to clip holders 856, counterclockwise rotation of caps 852 causes clips 846 to snap at their weakest points: narrowed regions 878. Vascular device 10 may then be removed from the patient to complete the procedure.

Although preferred illustrative embodiments of the present invention are described above, it will be evident to one skilled in the art that various changes and modifications may be made without departing from the invention. For example, with minor modifications, vascular device 10 may be configured to carry closure component 890 of FIG. 20, or any of a variety of alternative bioabsorbable and deformable clips. Proximal pins 854 may be formed integrally with caps 852, and distal pins 850 may be formed integrally with clip housing 816. Any number of clips 846 may be used to close the vascular puncture.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for introduction into an opening in a wall of a body lumen, comprising:
   a sheath having proximal and distal ends, the distal end having a size and shape for insertion into a body lumen, the distal end including first and second ports therein, the first port being disposed at a more distal location than the second port;
   an elongate member disposed within the sheath, the elongate member including a distal region configured for sealingly engaging an inner surface of the sheath, the elongate member including first and second openings in the distal region, the first and second openings being alignable with the first and second ports in the sheath; and
   first and second lumens extending distally from the proximal end of at least one of the sheath and the elongate member, the first and second lumens communicating with the first and second openings, respectively.

2. The apparatus of claim 1, further comprising a closure element slidably disposed on an exterior of the sheath, the closure element configured for engaging tissue adjacent the opening for closing the opening.

3. The apparatus of claim 1, further comprising a housing slidably disposed on the exterior of the sheath, the housing configured for releasably holding a closure element, the housing being actuable from a proximal end of the sheath for advancing the closure element distally during deployment of the closure element.

4. The apparatus of claim 1, wherein the first and second ports are axially aligned with one another.

5. The apparatus of claim 4, further comprising a marker on the proximal end of the tubular sheath, the marker having a predetermined peripheral orientation about the sheath for identifying the peripheral location of the first and second ports.

6. The apparatus of claim 1, wherein the elongate member is insertable into the sheath, and wherein the first and second ports are aligned with the first and second openings when the elongate member is fully inserted into the sheath.

7. The apparatus of claim 6, wherein the elongate member and the sheath include cooperating detents for securing the elongate member axially with respect to the sheath when the elongate member is fully inserted into the sheath.

8. The apparatus of claim 6, wherein the first lumen extends axially through the elongate member.

9. The apparatus of claim 6, wherein the second lumen comprises an annular lumen between the elongate member and the sheath.

10. The apparatus of claim 1, wherein the elongate member is insertable into the sheath, and wherein the first port is aligned with the first opening when the elongate member is inserted a first distance into the sheath, and wherein the second port is aligned with the second opening when the elongate member is inserted a second distance into the sheath.

11. The apparatus of claim 1, wherein the elongate member is rotatable within the sheath, and wherein the first port is aligned with the first opening when the elongate member is rotated to a first position within the sheath, and wherein the second port is aligned with the second opening when the elongate member is rotated to a second position within the sheath.

12. The apparatus of claim 1, wherein the first and second lumens extend within the elongate member between its proximal end and the first and second openings, respectively.

13. An apparatus for delivering a vascular closure element into engagement with tissue adjacent an opening into a body lumen, comprising:
   a sheath having proximal and distal ends and an exterior surface, the sheath including an interior surface defining a first lumen extending between the proximal and distal ends, and one or more ports in the distal end communicating with the first lumen;
   a housing slidably disposed on the exterior of the sheath, the housing being configured for releasably holding a closure element, the housing being actuable from a proximal end of the sheath for advancing the closure element distally during deployment of the closure element; and
   an elongate member insertable into the first lumen of the sheath, the elongate member including a distal region configured for sealingly engaging the interior surface of the sheath, thereby defining an annular region between the elongate member and the sheath proximal to the distal region, the annular region communicating with the one or more ports when the elongate member is fully inserted into the sheath.

14. The apparatus of claim 13, wherein the distal region of the elongate member is expandable between a contracted configuration and an enlarged configuration, the distal region sealingly engaging the interior surface of the sheath in the enlarged condition.

15. The apparatus of claim 13, further comprising a closure element releasably held by the housing, the closure element configured for engaging tissue adjacent-the opening for closing the opening.

16. The apparatus of claim 13, further comprising a backbleed port on the proximal end of the sheath, the backbleed port communicating with the first lumen.

17. The apparatus of claim 13, wherein the elongate member comprises a substantially flexible distal tip that extends from the distal end of the sheath when the elongate member is fully inserted into the sheath.

18. The apparatus of claim 13, wherein the one or more ports comprise a first port in the exterior surface of the sheath, and the sheath further comprises a second port located at a location distal from the first port.

19. The apparatus of claim 18, wherein the elongate member comprises a second lumen extending distally from its proximal end, the second lumen communicating with the second port when the elongate member is fully inserted into the sheath.

20. The apparatus of claim 19, wherein the elongate member includes a third lumen therein extending distally from its proximal end, the third lumen communicating with the first port when the elongate member is fully inserted into the sheath.

21. The apparatus of claim 13, further comprising a seal on the proximal end of the sheath, the seal slidably engaging the elongate member when it is inserted into the lumen, thereby sealing the lumen from proximal flow of fluid.

22. A method for positioning an introducer sheath in an opening in a wall of a body passage, the introducer sheath including a plurality of lumens extending distally from its proximal end and communicating with respective ports in its distal end, each port being disposed at a different distal location on the distal end, the method comprising:

inserting the distal end of the introducer sheath through a patient's skin towards the body passage via the opening; and positioning the distal end with respect to the body passage until one or more of the ports enter the body passage, whereupon fluid pressure within the body passage causes fluid from within the body passage to enter the respective one or more lumens communicating with the one or more ports in the body passage, thereby providing a visual indication of depth of insertion of the introducer sheath.

23. The method of claim 22, wherein the one or more ports are disposed in axial alignment with one another along the distal end, and wherein the step of positioning the distal end comprises rotating the introducer sheath about its longitudinal axis until the ports are in a predetermined orientation with respect to the body passage.

24. The method of claim 23, wherein the introducer sheath extends at a substantially lateral angle between the patient's skin and the body passage, and wherein the introducer sheath is rotated to position the ports in a desired rotational orientation.

25. The method of claim 22, further comprising advancing a closure element slidable on the introducer sheath distally to engage tissue within the opening adjacent the body passage.

26. An apparatus for introduction into an opening in a wall of a body lumen, comprising:

a sheath having proximal and distal ends, the distal end having a size and shape for insertion into a body lumen, the distal end including first and second ports therein, the second port being disposed at a more distal location than the first port; and an elongate member disposed within the sheath, the elongate member including a distal region having a size for sealingly engaging an inner surface of the sheath, the elongate member being movable with respect to the sheath for selectively opening and closing the first and second side ports to permit fluid flow therethrough to the proximal end of the sheath.

27. The apparatus of claim 26, wherein the elongate member at least partially defining a lumen extending from the proximal end of the sheath towards the distal region of the elongate member, and wherein the elongate member includes a region for selectively sealing the first and second ports in the sheath, whereby only one of the first and second ports communicates with the lumen.

28. The apparatus of claim 27, wherein the lumen is located within the elongate member.

29. The apparatus of claim 27, wherein the lumen is defined between the elongate member and the inner surface of the sheath.

30. The apparatus of claim 29, wherein the elongate member further comprises a second lumen therein having an inlet proximal to the distal region of the elongate member and a piston for sealingly engaging the inner surface of the sheath, the piston being located proximal to the inlet, whereby the second lumen communicates with the second side port when the elongate member is disposed at a first position, and the lumen between the elongate member and the inner surface of the sheath communicates with the first side port when the elongate member is disposed at a second position.

31. The apparatus of claim 30, wherein the elongate member is movable axially with respect to the sheath between the first and second positions.

32. The apparatus of claim 30, wherein the elongate member is rotatable with respect to the sheath between the first and second positions.

33. The apparatus of claim 26, further comprising a closure element slidably disposed on an exterior of the sheath, the closure element configured for engaging tissue adjacent the opening for closing the opening.

34. The apparatus of claim 26, further comprising a housing slidably disposed on the exterior of the sheath, the housing configured for releasably holding a closure element, the housing being actuable from a proximal end of the sheath for advancing the closure element distally during deployment of the closure element.

35. The apparatus of claim 26, wherein the first and second ports are axially aligned with one another.

36. The apparatus of claim 35, further comprising a marker on the proximal end of the tubular sheath, the marker having a predetermined peripheral orientation about the sheath for identifying the peripheral location of the first and second ports.

37. The apparatus of claim 26, wherein the elongate member and the sheath include cooperating detents for securing the elongate member with respect to the sheath at one or more desired positions.

* * * * *